(12) United States Patent
Hubbell et al.

(10) Patent No.: US 6,884,628 B2
(45) Date of Patent: *Apr. 26, 2005

(54) MULTIFUNCTIONAL POLYMERIC SURFACE COATINGS IN ANALYTIC AND SENSOR DEVICES

(75) Inventors: Jeffrey A. Hubbell, Zumikon (CH); Marcus Textor, Schaffhausen (CH); Donald L. Elbert, Zurich (CH); Stephanie Finken, Zurich (CH); Rolf Hofer, Biel (CH); Nicholas D. Spencer, Zollikon (CH); Laurence Ruiz-Taylor, Belmont, CA (US)

(73) Assignees: Eidgenossische Technische Hochschule Zurich, Zurich (CH); Universitat Zurich, Zurich (CH)

( * ) Notice: Subject to any disclaimer, the term of this patent is extended or adjusted under 35 U.S.C. 154(b) by 393 days.

This patent is subject to a terminal disclaimer.

(21) Appl. No.: 09/560,472

(22) Filed: Apr. 28, 2000

(65) Prior Publication Data

US 2002/0128234 A1 Sep. 12, 2002

Related U.S. Application Data

(60) Provisional application No. 60/184,616, filed on Feb. 24, 2000, provisional application No. 60/131,402, filed on Apr. 28, 1999, and provisional application No. 60/131,391, filed on Apr. 28, 1999.

(51) Int. Cl.$^7$ .................. G01N 33/53; G01N 33/543
(52) U.S. Cl. .................. 436/518; 427/2.1; 427/2.11; 427/2.12; 427/2.13; 427/8; 427/207.1; 427/256; 427/299; 427/304; 427/331; 427/402; 427/404; 427/414; 427/419.1; 427/419.5; 435/4; 435/7.1; 435/7.92; 435/174; 435/176; 435/177; 435/178; 435/179; 435/180; 435/183; 435/287.1; 435/287.2; 435/287.7; 435/287.8; 435/287.9; 435/815; 435/961; 435/969; 436/524; 436/528; 436/529; 436/530; 436/819; 436/823
(58) Field of Search .................. 427/2.1, 2.11, 427/2.12, 2.13, 8, 207.1, 256, 299, 304, 331, 402, 404, 414, 419.1, 419.5; 435/4, 7.1, 7.92, 174, 176, 177, 178, 179, 180, 183, 287.1, 287.2, 287.7, 287.8, 287.9, 815, 961, 969; 436/518, 524, 528, 529, 530, 819, 823

(56) References Cited

U.S. PATENT DOCUMENTS

4,822,867 A * 4/1989 Erhan .................. 527/200

(Continued)

FOREIGN PATENT DOCUMENTS

EP 0 561 239 A1 9/1993

(Continued)

OTHER PUBLICATIONS

Humphries et al. The use of graft copolymers to inhibit the adhesion of bacteria to solid surfaces. FEMS Microbiology Ecology. (1987) vol. 45, pp. 297–304.*

(Continued)

*Primary Examiner*—Long Le
*Assistant Examiner*—Kartic Padmanabhan
(74) *Attorney, Agent, or Firm*—Pabst Patent Group LLP

(57) ABSTRACT

Multifunctional, polyionic copolymers with molecular architectures and properties optimized for specific applications are synthesized on/or applied to substrate surfaces for analytical and sensing purposes. The coatings are particularly useful for suppression of non-specific interaction, adsorption or attachment of molecular or ionic components present in an analyte solution. Chemical, biochemical or biological groups that are able to recognize, interact with and bind specifically to target molecules in the material containing the analyte to be detected can be coupled to, integrated into, or absorbed to the multifunctional copolymers. These multifunctional copolymer coatings are compatible with a variety of different established methods to detect, sense and quantify the target molecule in an analyte. The multifunctional copolymer coatings typically include brush copolymers based on a polycationic or polyanionic (jointly referred to herein as 'polyionic') backbone with side chains that control interaction with the environment, such as poly(ethylene glycol) or poly(ethylene oxide)-based side chains that decrease cellular adhesion, and analyte-specific side chains. They can be used to pattern the surfaces into non-adhesive and specifically adhesive areas by applications of known techniques such as microfluidic or contact printing techniques.

13 Claims, 9 Drawing Sheets

U.S. PATENT DOCUMENTS

| | | | | | |
|---|---|---|---|---|---|
| 4,886,836 | A | * | 12/1989 | Gsell et al. | 521/53 |
| 5,250,613 | A | * | 10/1993 | Bergstrom et al. | 525/54.1 |
| 5,330,911 | A | * | 7/1994 | Hubbell et al. | 435/240.243 |
| 5,344,455 | A | * | 9/1994 | Keogh et al. | 623/11 |
| 5,414,075 | A | * | 5/1995 | Swan et al. | 568/333 |
| 5,459,054 | A | * | 10/1995 | Skjak-Braek et al. | 435/178 |
| 5,462,990 | A | | 10/1995 | Hubbell et al. | |
| 5,470,731 | A | * | 11/1995 | Cochrum | 435/182 |
| 5,507,804 | A | * | 4/1996 | Llanos | 623/11 |
| 5,512,492 | A | * | 4/1996 | Herron et al. | 436/518 |
| 5,543,326 | A | * | 8/1996 | Heller et al. | 435/287.9 |
| 5,573,934 | A | | 11/1996 | Hubbell et al. | |
| 5,578,442 | A | * | 11/1996 | Desai et al. | 435/1.1 |
| 5,626,863 | A | | 5/1997 | Hubbell et al. | |
| 5,627,233 | A | | 5/1997 | Hubbell et al. | |
| 5,629,213 | A | * | 5/1997 | Kornguth et al. | 436/518 |
| 5,658,622 | A | * | 8/1997 | Berlin et al. | 428/34.2 |
| 5,661,025 | A | * | 8/1997 | Szoka, Jr. et al. | 435/172.3 |
| 5,711,915 | A | * | 1/1998 | Siegmund et al. | 422/68.1 |
| 5,776,747 | A | * | 7/1998 | Schinstine et al. | 435/177 |
| 5,866,322 | A | * | 2/1999 | Jou et al. | 435/5 |
| 5,916,585 | A | * | 6/1999 | Cook et al. | 424/426 |
| 5,932,462 | A | * | 8/1999 | Harris et al. | 435/188 |
| 6,093,558 | A | * | 7/2000 | Seed et al. | 435/176 |
| 6,121,027 | A | * | 9/2000 | Clapper et al. | 435/180 |
| 6,207,749 | B1 | * | 3/2001 | Mayes et al. | 524/731 |
| 6,235,340 | B1 | * | 5/2001 | Lee et al. | 427/2.12 |
| 6,248,127 | B1 | * | 6/2001 | Shah et al. | 623/1.15 |
| 6,258,870 | B1 | * | 7/2001 | Hubbell et al. | 522/26 |
| 6,265,016 | B1 | * | 7/2001 | Hostettler et al. | 427/2.11 |
| 6,284,503 | B1 | * | 9/2001 | Caldwell et al. | 435/181 |
| 6,287,558 | B1 | * | 9/2001 | Lanza et al. | 424/93.7 |
| 6,291,216 | B1 | * | 9/2001 | Muller et al. | 435/178 |
| 6,303,136 | B1 | * | 10/2001 | Li et al. | 424/424 |
| 6,303,179 | B1 | * | 10/2001 | Koulik et al. | 427/2.26 |
| 6,306,243 | B1 | * | 10/2001 | Clark et al. | 156/331.2 |
| 6,306,659 | B1 | * | 10/2001 | Parce et al. | 422/55 |
| 6,348,322 | B1 | * | 2/2002 | Strittmatter | 422/55 |

FOREIGN PATENT DOCUMENTS

| | | | |
|---|---|---|---|
| WO | WO 92/06678 | * | 4/1992 |
| WO | WO 93/07298 A1 | | 4/1993 |
| WO | WO 93/24076 A1 | | 12/1993 |
| WO | WO 94/27137 A2 | | 11/1994 |
| WO | WO-98/46351 A1 | * | 10/1998 |
| WO | WO 98/47948 A1 | | 10/1998 |
| WO | WO 98/47948 | * | 10/1998 |

OTHER PUBLICATIONS

Arnold & Rechnitz, "Selectivity enhancement of a tissue-based adenosine-sensing membrane electrode," *Anal. Chem.* 53(3):515–8 (1981).

Borenfreund, "Comparisons of two in vitro cytotoxicity assays—the neutral reds (NR) and tetrazolium MTT tests," *Toxic. In Vitro* 2(1):1–6 (1988).

Boyan, et al., "Effect of titanium surface characteristics on chondrocytes and osteoblasts in vitro," *Cell. Mater.* 5(4):323–35 (1995).

Burmeister, et al., "Application of total internal reflection fluorescence microscopy to study cell adhesion to biomaterials," *Biomaterials* 19(4–5):307–25 (1998).

Chittur, "Surface techniques to examine the biomaterial-host interface: an introduction to the papers," *Biomaterials* 19(4–5):301–5 (1998).

Divies, "Remarks on ethanol oxidation by an "Acetobacter xylinum" microbial electrode," *Ann. Microbiol.* 126(2):175–86 (1975).

Elbert & Hubbell, "Self–assembly and steric stabilization at heterogeneous, biological surfaces using adsorbing block copolymers," *Chem. Biol.* 5(3):177–83 (1998).

Etcheverry, et al., "Insulin–mimetic action of vanadium compounds on osteoblast–like cells in culture," *Arch. Biochem. Biophys.* 338(1):7–14 (1997).

Fredriksson, et al., "The piezoelectric quartz crystal mass and dissipation sensor: A means of studying cell adhesion," *Langmuir* 14:248–251 (1998).

Honig, et al., "Fluorescent carbocyanine dyes allow living neurons of identified origin to be studied in long–term cultures," *J. Cell. Biol.* 103(1):171–87 (1986).

Kodama, et al., Establishment of a clonal osteogenic cell line from newborn mouse calvaria, *Jpn. J. Oral Biol.* 23:899–901 (1981).

Labarca, et al., "A simple, rapid, and sensitive DNA assay procedure," *Anal. Biochem.* 102(2):344–52 (1980).

Luegmayr, et al., "Effects of triiodothyronine on morphology, growth behavior, and the actin cytoskeleton in mouse osteoblastic cells (MC3T3-E1)," *Bone.* 18(6):591–9 (1996).

Macholan & Schanel, "Mushroom tissue–based biocatalytic electrode for determining phenols," *Biologia* 39(12):1191–1197 (1984).

Mackie, et al., "Modulation of osteoblast behaviour by tenascin," *J. Cell. Sci.* 109 ( Pt 6):1597–604 (1996).

Massia & Hubbell, "Vascular endothelial cell adhesion and spreading promoted by the peptide REDV of the IIICS region of plasma fibronectin is mediated by integrin alpha 4 beta 1," *J. Biol. Chem.* 267(20):14019–26 (1992).

McConnell, et al., "The cytosensor microphysiometer: biological applications of silicon technology," *Science* 257(5078):1906–12 (1992).

McKay, et al., "Interactions of orthopaedic metals with an immortalized rat osteoblast cell line," *Biomaterials.* 17(13):1339–44 (1996).

Moreau, et al., "Free radicals and side products released during methylmethacrylate polymerization are cytotoxic for osteoblastic cells," *J. Biomed. Mater. Res.* 40(1):124–31 (1998).

Mosmann, "Rapid colorimetric assay for cellular growth and survival: application to proliferation and cytotoxicity assays," *J. Immunol. Methods.* 65(1–2):55–63 (1983).

Mulchandini, et al., "Biosensor for direct determination of organophosphate nerve agents using recombinant *Escherichia coli* with surface–expressed organophosphorus hydrolase. 1. Potentiometric microbial electrode," *Anal. Chem.* 70(19):4140–5 (1998).

Ragnarson, et al., "Labeling with fluorescent carbocyanine dyes of cultured endothelial and smooth muscle cells by growth in dye–containing medium," *Histochemistry.* 97(4):329–33 (1992).

Ramsden, et al., "Optical method for measurement of number and shape of attached cells in real time," *Cytometry* 19(2):97–102 (1995).

Ramsden, Review of new experimental techniques for investigating random sequential adsorption, *Journal of Statistical Physics* 73 (5/6):853–877 (1993).

Rechnitz, et al., "Glutamine–selective membrane electrode that uses living bacterial cells," *Science* 199(4327):440–1 (1978).

Rodahl, et al., "Simultaneous frequency and dissipation factor QCM measurements of bimolecular adsorption and cell adhesion," *Faraday Discuss* 107:229–246 (1997).

Sudo, et al. "In vitro differentiation and calcification in a new clonal osteogenic cell line derived from newborn mouse calvaria," *J. Cell. Biol.* 96(1):191–8 (1983).

Yamamoto, "Cytotoxicity evaluation of 43 metal salts using murine fibroblasts and osteoblastic cells," *J. Biomed. Mater. Res.* 39(2):331–40 (1998).

* cited by examiner

IMMOBILIZED RECOGNITION MOLECULE

FUNCTIONALIZED POLYMER-GRAFTED PEG

SPECIFIC ADSORBED TARGET MOLECULE

BIOLOGICAL OR NON-BIOLOGICAL MOLECULE

MULTIFUNCTIONAL POLYMERIC SURFACE COATINGS IN ANALYTIC AND SENSOR DEVICES

This application claims priority to U.S. Ser. No. 60/184,616 filed Feb. 24, 2000, U.S. Ser. No. 60/131,402 filed Apr. 28, 1999 and U.S. Ser. No. 60/131,391 filed Apr. 28, 1999.

BACKGROUND OF THE INVENTION

This application is in the general area of polymeric coating materials which can be applied to surfaces of substrates used in analytical and sensing devices to promote specific recognition of the target analyte while minimizing non-specific adsorption of other molecules in the sampling solution.

There is a need to improve the selectivity and sensitivity of bioaffinity and diagnostic sensors, especially for use in screening assays and libraries for DNA/RNA and proteins. A common approach to diagnostic sensor design involves the measurement of the specific binding of a particular component of a physiological sample. Typically, physiological samples of interest (e.g. blood samples) are complex mixtures of many components that all interact to varying degrees with surfaces of diagnostic sensors. However, the aim of a diagnostic sensor is to probe only the specific interaction of one component while minimizing all other unrelated interactions. In the case of sensors in contact with blood, proteins, glycoproteins and/or saccharides, as well as cells, often adsorb non-specifically onto the sensor surface. This impairs both selectivity and sensitivity, two highly important performance criteria in bioaffinity sensors.

A variety of materials and surfaces is used in analytical and sensor devices, such as glass, silicon wafers, metals or metallized surfaces and metal oxides as bulk or coating materials. The choice of the materials is closely related to the particular sensing technique used. If surface plasmon resonance is used as an analytical or sensing method, the chips will consist of a substrate coated with a metal such as gold. In the case of analytical or sensor chips to be used in combination with specific optical detection sensor chips to be used in combination with specific optical detection techniques, such as fluorescence spectroscopy, optical waveguide techniques or a combination of the two, optically transparent substrates and/or coatings are often needed. Metal oxides or metal oxide coatings are particularly suitable in such cases, in view of their stability, inertness and optical transparency. Polymeric materials are traditionally used for applications in lateral flow assays or multiwell plate assays. Glass or silicon based materials are often used for capillary electrophoresis applications. Both polymeric and glass type materials are used in fiberoptics.

Independent of the analytical or sensing technique used, there is a basic need for surface modification of the chips, as these materials and surfaces do not have the necessary properties in terms of controlled adsorption phenomena in a given detection or sensing application. There is a need for simple, cost-effective treatment materials and methods that effectively reduce non-specific interactions at or adsorption onto metal oxide-based sensor surfaces while introducing a specific binding interaction with the target analyte. Such specific recognition, binding and detection are often achieved through key-lock type of chemical or biological interactions such as antibody-antigen interactions.

The application of multifunctional polymers in implants can be employed to control biological interactions that determine a bioresponse to an implant. Here the same principles of recognition, specificity and suppression of nonspecific adsorption are relevant. An example is the selection of attaching cells in a biological response, where suppression of nonspecific adsorption of proteins from the body fluids can suppress the nonspecific attachment of cells and the inclusion of biospecific recognition ligands, such as adhesion peptides, can enhance the attachment of a specific cell population or subpopulation.

The use of functional polymers and copolymers is an approach often chosen in the biomaterial area to modify surface properties or cell-to-cell interactions. For example, U.S. Pat. Nos. 5,573,934 and 5,626,863 to Hubbell et al. disclose hydrogel materials containing a water-soluble region such as polyethylene glycol and a biodegradable region, including various biodegradable polymers such as polylactide and polyglycolide, terminated with photopolymerizable groups such as acrylates. These materials can be applied to a tissue surface and polymerized, for example, to form tissue coatings. These materials are adhered to tissue surfaces by polymerizing the photopolymerizable groups on the materials after they have been applied to the tissue surface. U.S. Pat. Nos. 5,462,990 and 5,627,233 to Hubbell et al. disclose multifunctional polymeric materials for use in inhibiting adhesion and immune recognition between cells and tissues. The materials include a tissue-binding component (polycation) and a tissue non-binding component (polyanion). In particular, Hubbell discloses various PEG/PLL copolymers, with molecular weights greater than 300, with structures that include AB copolymers, ABA copolymers, and brush-type copolymers. These polymers are being commercially developed for use as tissue sealants and to prevent surgical adhesions. WO 98/47948 'Multifunctional Polymeric Tissue Coatings' by Hubbell et al. describes another class of polymer, grafted polyionic copolymers that are able to attach to biological and non-biological samples in order to control cell-surface and cell-cell and tissue-surface interactions in biomedical applications. These materials have not been used to coat devices or devices for implantation, however, especially devices having metal oxide or other surfaces which may not adhere well to receptors or other ligands used for sensing or analysis.

It is therefore an object of the present invention to provide materials which can be used to control and modify cell-surface and cell-cell interactions, especially on the surface of devices and implants.

It is a further object of the present invention to provide methods for application of these materials to a substrate which is rapid, inexpensive, and flexible.

It is another object of the present invention to provide a stable polymeric material that can be applied simply, quickly and cost-effectively to charged surfaces of analytical devices and sensor chips for applications where it is essential to establish a specific binding interaction while preventing the unwanted non-specific interactions that typically occur at surfaces in contact with physiological and other types of samples. analytical or diagnostic devices, culture surfaces, sensor chips, and implants.

SUMMARY OF THE INVENTION

Multifunctional, polyionic copolymers with molecular architectures and properties optimized for specific applications are synthesized on/or applied to substrate surfaces for analytical and sensing purposes. The coatings are particularly useful for suppression of non-specific interaction, adsorption or attachment of molecular or ionic components present in an analyte solution. Chemical, biochemical or biological groups can be coupled to, integrated into or absorbed to the multifunctional polymer that are able to recognize, interact with and bind specifically to target molecules in the material containing the analyte to be detected. These multifunctional polymer coatings are compatible with a variety of different established methods to detect, sense and quantify the target molecule in an analyte. These materials can also be used to modulate biological interactions upon substrate surfaces for use as selective implant surfaces that resist cell attachment and may optionally promote the attachment of specific cell types or induce a particular cellular behavior.

The multifunctional polymer coatings typically include brush copolymers based on a polycationic or polyanionic (jointly referred to herein as 'polyionic') backbone with side chains that control interaction with the environment, such as poly(ethylene glycol) or poly(ethylene oxide)-based side chains that decrease cellular adhesion (referred to herein as "non-interactive" side chains or polymers), and analyte-specific side chains. Examples of polyionic backbones are poly(amino acids) such as poly(lysine) and poly(arginine) with positive charges at physiological pH and poly(glutamic acid) and poly(aspartic acid) with negative charges at physiological pH. The poly(ethylene glycol) (PEG) chains are highly water soluble and highly flexible. PEG chains have an extremely high motility in water and are essentially non-ionic in structure. They are well known for their weak interaction with both molecules and ions and, if attached to the surface in suitable form (molecular weight, density, orientation), they decrease adhesiveness or adsorption to the surface, such as protein resistance in contact with blood or serum. The choice of positively charged (cationic) or negatively charged (anionic) backbones of such PEO-grafted backbones is related to the fact that surfaces often possess a positive or negative charge when exposed to an aqueous environment. In particular, metal oxides or metal oxide coatings exposed to an aqueous analyte spontaneously acquire a negative charge at pH above the isoelectric point (IEP) and positive charges at pH below the isolectric point of the particular oxide chosen. At pH of 7 (neutral solution) for example, niobium oxide, tantalum oxide or titanium oxide will be negatively charged, while aluminium oxide at pH 7 is positively charged. In other cases, such as a noble metal surface, the surface may not be (sufficiently) charged to allow for complete polymer adsorption through electrostatic interaction. In such cases the surface may be treated to introduce positive or negative charges. For example, carboxylate groups may be introduced through self-assembly of carboxy-terminated long-chain alkanethiols on gold or silver to induce a positive charge at a pH above 4. Alternatively, amino groups that are positively charged at pH below 9 may be introduced on gold or silver surfaces, e.g. through self-assembly of amino-terminated alkanethiols. The PEG-grafted polyionic copolymer can be further modified by introducing functional groups at or near the terminal (free end) position of the PEG chains. These groups allow further functionalization and incorporation of adhesive sites or recognition entities that serve as the capture moiety in an analytical or sensing assay.

Non-modified and modified copolymers can be used singly, consecutively or as a mixture. They can be used to pattern the surfaces into non-adhesive and specifically adhesive areas by applications of known techniques such as microfluidic or contact printing techniques.

Although described primarily with reference to substrates or surfaces of analytical or sensing devices, where the material the copolymer is applied to is a metal or metal oxide, polymer substrates can also be used, especially when patterning is not involved in the bioanalytical concept. For example, many surfaces employed in ELISA systems and in cell culture systems are polymers. Polystyrene is a very convenient such polymer, because of its optical clarity, its ease of processability, and its low expense. Polystyrene can be readily functionalized to introduce surface charge, either negative or positive, to create the appropriate charged substrate. For example, exposure of polystyrene to air or oxygen plasmas is well known to create stable modified surfaces that include anionic groups, and exposure to ammonia plasmas is well known to create stable modified surfaces that include cationic groups at typical operating pH. Thus, it is readily possible to employ such polymers, and also many other polymers either with anionic or cationic groups that are intrinsic to their polymer structure or that are introduced by a surface modification procedure such as a plasma process, in both bioanalytical systems based on noncellular and cellular approaches. Such noncellular approaches include ELISA systems, where the multifunctional polymer is adsorbed to the polymer substrate and an antibody is then chemically coupled to the multifunctional polymer. Likewise, in cell-mediated systems, the polymer may be adsorbed and then coupled to a cell-interacting biomolecule, such as an adhesion peptide, or alternatively the cell-interacting biomolecule may be coupled prior to adsorption. In both ELISA systems and in cell-culture systems, simple and inexpensive polymer substrates may be advantageous.

Both metal and polymer substrates may also be useful in the context of medical implants. For example, a number of important implants are constructed from metals, such as titanium or stainless steel, including orthopedic implants and cardiovascular implants. Likewise, a number of important implants are constructed from polymers, such as silicone rubber and polyesters, both of which can be treated by plasma processes or other processes to introduce surface charge. The polymeric materials can also be advantageous when used to coat these materials.

BRIEF DESCRIPTION OF THE FIGURES

FIG. 1A is the chemical structure of the polycationic poly(L-lysine)-g-poly(ethylene glycol) (PEG-g-PLL) for surface modification of negatively charged surfaces; FIG. 1B is a chemical structure of a PEG-g-PLL polymer, functionalized with biotin at the terminus of part of the PEG side chains; FIG. 1C is the chemical structure of the polyanionic poly(L-glutamic acid)-g-poly(ethylene glycol) (PEG-g-PLG) for surface modification of positively charged surfaces; and FIG. 1D is a chemical structure of a (PEG-g-PLG) polymer functionalized with biotin at the terminus of part of the PEG side chains.

DETAILED DESCRIPTION OF THE INVENTION

Figure 1A:
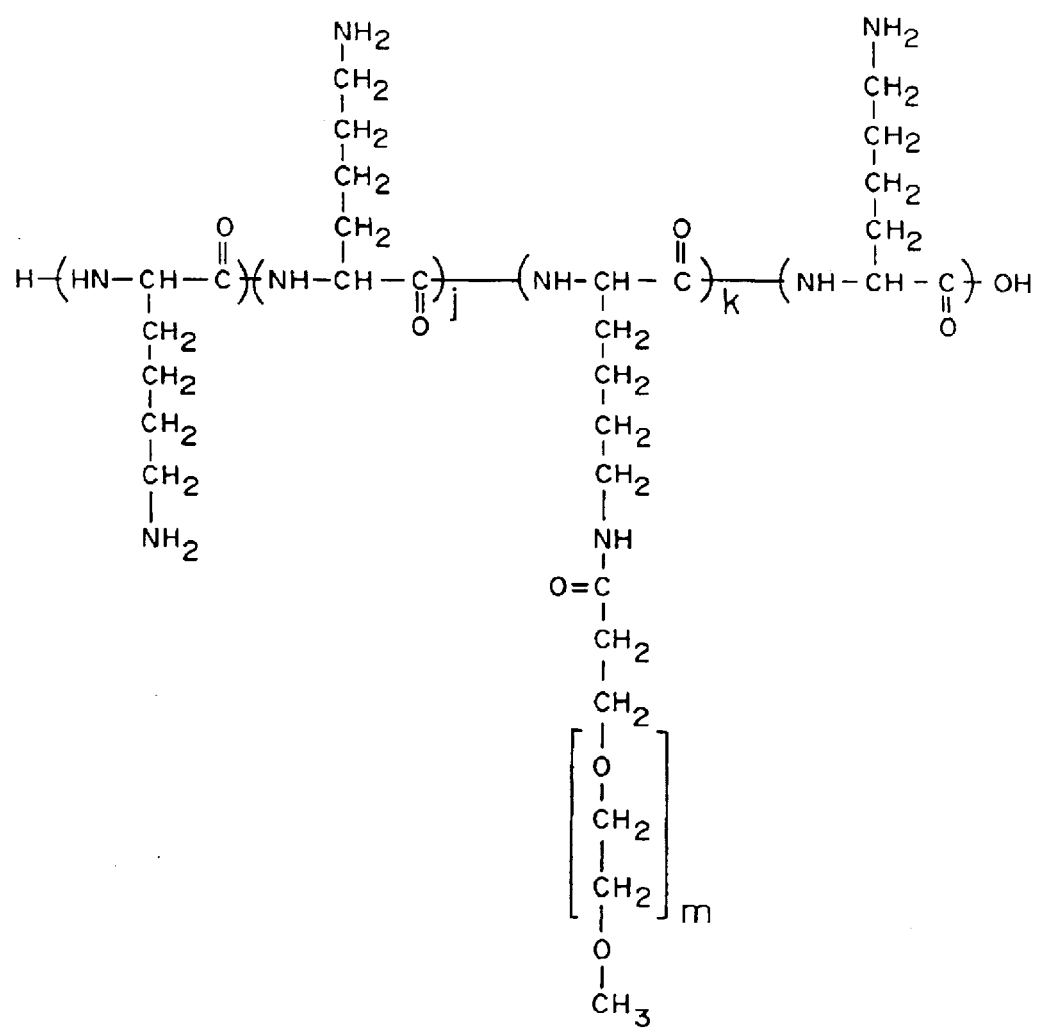
FIGS. 1A–1D are the chemical structures of polymers described herein.
Figure 1B:
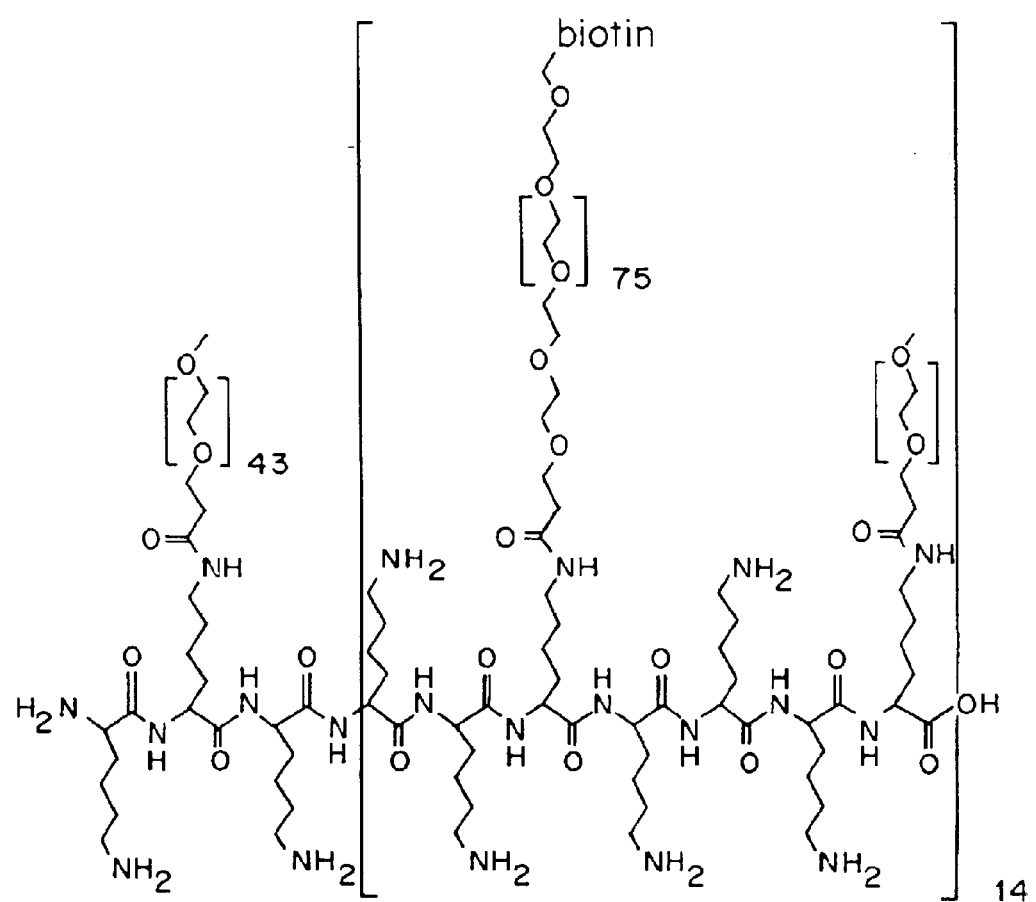
Figure 1C:
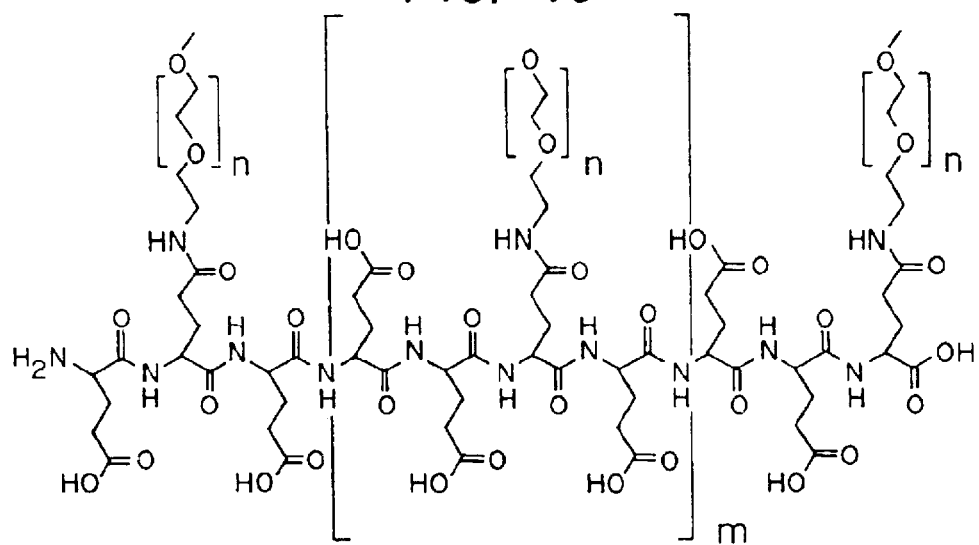
Figure 1D:
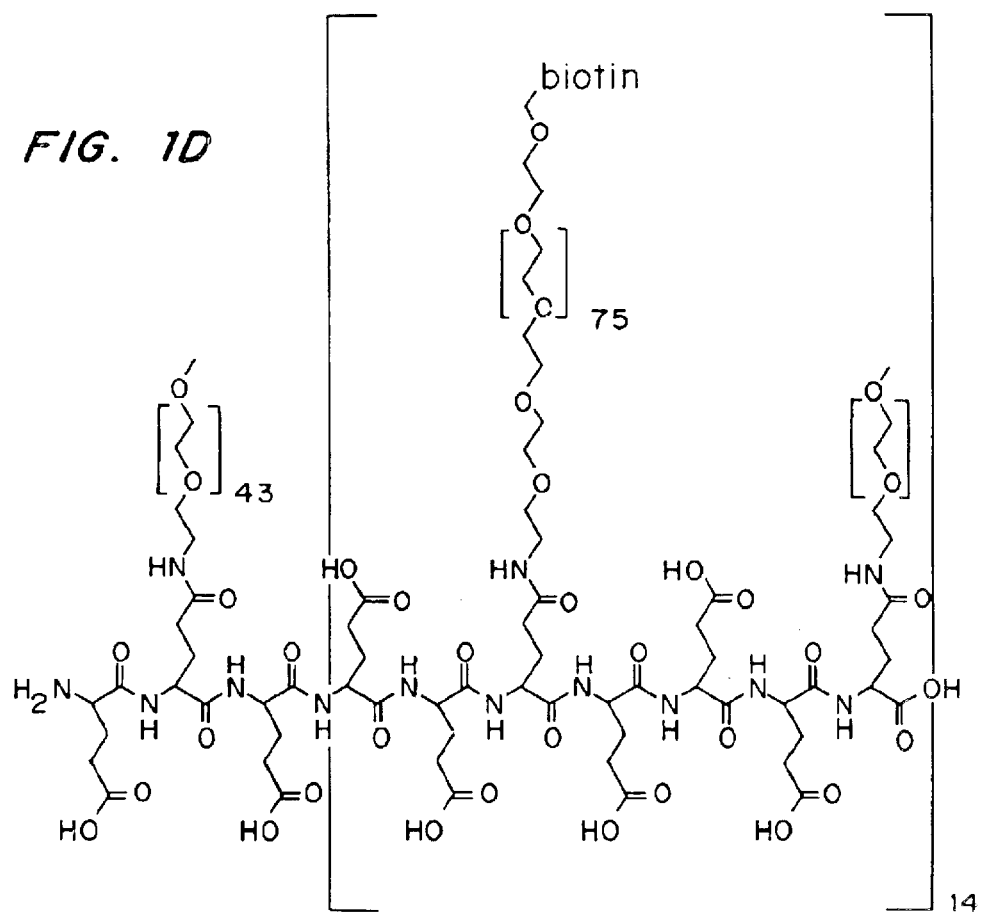
Figure 2A:
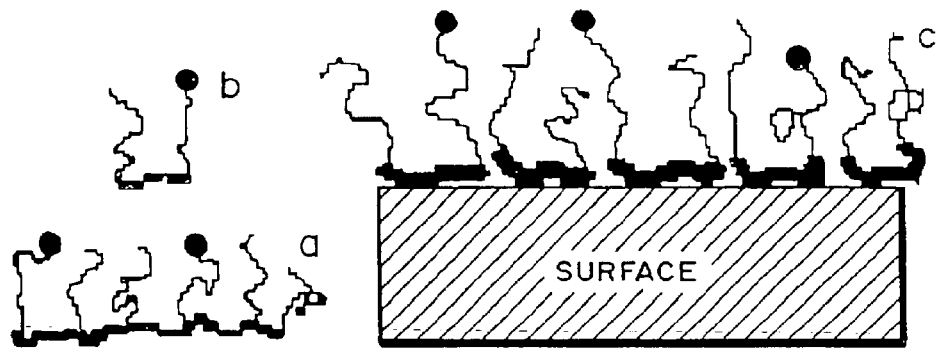
FIG. 2A is a schematic of adsorbed multifunctional polymers to render surfaces protein- and cell-resistant. Graft copolymers (a) and block copolymers (b) are formed from cationic components (heavy line) and poly(ethylene glycol) (light line). Specific peptides are attached to the tips of the poly(ethylene glycol) chains (dots).
Figure 2B:
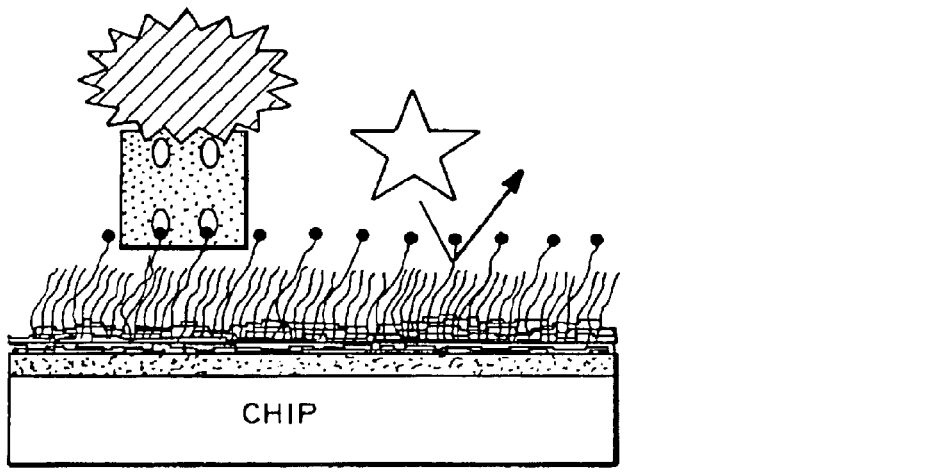
FIG. 2B is a schematic drawing of a bioaffinity assay based on a chip surface coated with a copolymer-monolayer. The recognition molecule is immobilized by interaction with the terminal function of the polymer-grafted PEG. The surface can be used for the specific binding of target molecules (left), while the PEG-layer prevents non-specific adsorption of biological and non-biological components of the analyte.
Figure 2B:
Figure 2B:
Figure 2B:
Figure 2B:

Polycationic and polyanionic copolymers that adsorb to (oppositely) charged surfaces of substrates and devices ('chips') for analytical and sensing applications are disclosed. These serve three functions: (1) charged sites in the backbone attach the polymer to substrate surface via interactions between oppositely charged groups on the substrate and the backbones; (2) grafted side chains that form a dense structure such as a brush make the surface non-interactive, i.e., prevent the adsorption of molecules or ions out of an analyte onto the surface (referred to herein as "non-interactiveness", "non-adhesiveness", or "resistance to non-specific adsorption") and (3) functional groups allow the incorporation of recognition units for specific detection and sensing of low concentrations of analytes (referred to herein as "functional recognition sites"). Although described primarily with reference to chips, these materials can also be used to coat polymeric materials used in immunoassay and combinatorial library screening techniques, usually polymers such as polystyrene or polycarbonate, or implants such as bone prosthetics, screws, rivits, and vascular grafts, which are typically formed of metals and/or polymeric materials.

Treatment of the surface or substrate materials with the copolymers makes the surface completely or nearly completely resistant to (unwanted) non-specific adsorption. Suitable functional, reactive or interactive groups can also be introduced into the copolymers. As used herein, these functional or reactive or interactive copolymers are referred to as 'modified copolymers'. These reactive groups can be used for the further functionalization of the polymer, i.e. the adsorption or attachment of specific molecules such as antibodies, antigens, enzymes, oligonucleotides, single-stranded DNA or RNA moieties. The latter molecules immobilized at the surface in a sea of non-interactiveness are able to sense specifically target molecules using established analytical or sensing techniques. The multifunctional copolymers that include the specific recognition unit or functional molecules are referred to herein as 'functionalized polymers'.

Procedures for treatment of the substrates and surfaces with the non-modified, modified and/or functionalized polyionic copolymers are also disclosed.

Preferred analytical or sensing detection procedures and applications of the chips modified and functionalized are described in detail below.

I. Compositions of Non-Interactive Polymer-grafted Polyionic Copolymers.

Block copolymers are defined as copolymers in which a polymeric block is linked to one or more other polymeric blocks. This is distinguished from random copolymers, in which two or more monomeric units are linked in random order to form a copolymer. Brush copolymers (as in a bottlebrush) are copolymers, which have a backbone of one composition and bristles of another. These copolymers are also known as comb copolymers. The terms brush and comb are used interchangeably. Dendritic polymers, also known as dendrimers or starburst polymers, are polymers which include a core molecule which is sequentially reacted with monomers with three or more reactive groups, such that at each sequential coupling step, the number of reactive groups at the ends of the polymer increases, usually exponentially. A dendron is a subunit of a dendrimer, the cone shaped structure resulting from sequential reactions starting with a core containing only reactive group. As used herein, molecular weight refers to weight-average molecular weight, unless otherwise specified.

The preferred non-interactive polymer is poly(ethylene glycol), or "PEG". For ease of description, the general description of the graft copolymers refers to PEG rather than "non-interactive polymer".

The co-polymers can be brush copolymers (as in a bottlebrush, with a backbone of one composition and bristles of another) with a charged polymeric backbone, such as a poly(amino acid). The first example refers to poly-L-lysine (PLL) and bristles of polyethylene glycol (PEG). The molecular weight of the PLL is between 1,000 and 1,000,000, preferably greater than 100,000, more preferably, between 300,000 and 800,000. The molecular weight of the PEG is between 500 and 2,000,000, more preferably between 1,000 and 100,000. Various surfaces binding polyionic polymers can be substituted for PLL, and various non-interactive polymers can be substituted for PEG.

A. Non-Interactive Polymers

The term 'non-interactive' is used here in the context of the application of such molecules for coating analytical and sensor devices and means that the non-interactive polymer in the surface-adsorbed copolymer reduces the amount of (non-specific) adsorption of molecules such as inorganic ions, peptides, proteins, saccharides and other constituents contained in typical analytes of biological or non-biological origin. Alternatives to the wording non-interactive are non-adhesive, adsorption-resistive or adsorption-repulsive in the context of non-specific adsorption.

PEG is a preferred material as the non-interactive polymer. The choice of the grafting ratio (number of PEG chains to number of monomers in the polymeric polyionic backbone) is important as it determines, when adsorbed onto the device surface, the degree of the desired non-adhesiveness. For PEG with a MW of 5000, the optimal graft ratio is between 1 PEG chain for every 3 to 10, preferably 4 to 7, lysine subunits for analytical or sensing applications, and may be adjusted based on desired properties. The optimum grafting ratio however depends on the MW of the PEG as well as on the specific applications. For example, if the MW of the PEG chains to be grafted onto the PLL backbone is 2000, the ratio of PEG units to PLL units should be between 2 and 8, preferentially between 3 and 5. The properties of sensor surfaces coated with PLL-PEG of different architecture are discussed in Example 1.

Suitable non-interactive polymers include mixed polyalkylene oxides having a solubility of at least one gram/liter in aqueous solutions such as some poloxamer nonionic surfactants, neutral water-soluble polysaccharides, polyvinyl alcohol, poly-N-vinyl pyrrolidone, non-cationic poly(meth)acrylates, many neutral polysaccharides, including dextran, ficoll, and derivatized celluloses, polyvinyl alcohol, non-cationic polyacrylates, such as poly(meth)acrylic acid, and esters amide and hydroxyalkyl amides thereof, and combinations thereof.

B. Polyionic Backbone Polymers

Suitable polycationic blocks include natural and unnatural polyamino acids having net positive charge at or close to neutral pH, positively charged polysaccharides, and positively charged synthetic polymers. Representative polycationic blocks include monomeric units selected from the group consisting of lysine, histidine, arginine and omithine. Representative positively charged polysaccharides include chitosan, partially deacetylated chitin, and amine-containing derivatives of neutral polysaccharides. Representative positively charged synthetic polymers include polyethyleneimine, polyamino(meth)acrylate, polyaminostyrene, polyaminoethylene, poly(aminoethyl) ethylene, polyaminoethylstyrene, and N-alkyl derivatives thereof. Representative polycationic materials include natural and unnatural polyamino acids having net positive charge at neutral pH, positively charged polysaccharides, and positively charged synthetic polymers. Examples of suitable polycationic materials include polyamines having amine groups on either the polymer backbone or the polymer sidechains, such as poly-L-lysine and other positively charged polyamino acids of natural or synthetic amino acids or mixtures of amino acids, including poly(D-lysine), poly(omithine), poly(arginine), and poly(histidine), and nonpeptide polyamines such as poly(aminostyrene), poly(aminoacrylate), poly (N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methylacrylamidopropyltrimethyl ammonium chloride), and natural or synthetic polysaccharides such as chitosan. Polylysine is a preferred material.

In general, the polymers must include at least five charges, and the molecular weight of the polyionic material must be sufficient to yield the desired degree of binding to the surface of the analytical or sensing device, having a molecular weight of at least 1000 g/mole.

For example, PEG reacted with polyethylene imine with a molecular weight greater than 10,000 will have approximately the same physical properties as the PEG/PLL copolymers described herein. Polyhydroxyethyl methacrylate can be reacted with a suitable stoichiometric ratio of a reagent such as tresyl or tosyl chloride (an activating agent), which converts some of the hydroxy groups to leaving groups. These leaving groups can be reacted with polycationic polymers, for example, polyaminoethyl methacrylate with a molecular weight greater than 10,000, to yield a high-molecular-weight polymer. A suitable stoichiometric ratio is one mole activating agent per mole of polyhydroxyethyl methacrylate, and one mole activated polyhydroxyethyl methacrylate per every 3 to 9, preferably 5 to 7 moles of reactive groups on polyaminoethyl methacrylate. Suitable cationic polymers are those that, when combined with a suitable non-interactive polymer, have roughly the same physical properties as the PEG/PLL copolymers described herein.

Suitable polyanionic blocks include natural and synthetic polyamino acids having net negative charge at neutral pH. A representative polyanionic block is poly(glutamic acid), which contains carboxylic acid side chains with a negative charge at pH 7. Glycolic acid is just one example. It may be replaced by other natural or unnatural monomers that can be polymerized and contain a side functional group with negative charge at or near neutral pH, for example, any polymer having carboxylic acid groups attached as pendant groups. Suitable materials include alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose and crosmarmelose, synthetic polymers and copolymers containing pendant carboxyl groups, such as those containing maleic acid or fumaric acid in the backbone. Polyaminoacids of predominantly negative charge are particularly suitable. Examples of these materials include polyaspartic acid, polyglutamic acid, and copolymers thereof with other natural and unnatural amino acids. Polyphenolic materials such as tannins and lignins can also be used. Preferred materials include alginate, pectin, carboxymethyl cellulose, heparin and hyaluronic acid.

In general, the molecular weight of the polyanionic material must be sufficiently high to yield strong adhesion to the positively charged analytical or sensor device surface. The lengths of the polycationic and polyanionic materials which would result in good blockage of adhesive interactions may be determined by routine experimentation. It should be understood that "good" is a word that must be defined by the requirements of the particular situation at hand, e.g., how long binding is required and how complete a non-interactivness is required by the particular sensing application.

Apart from carboxylate end groups, sulfate, sulfonate, phosphate or groups that apart from being negatively charged have cation-chelating properties such as ethylendiamintetraacetic acid (EDTA) or nitrilotrisacetic acid (NTA) can be used as well. The term 'cation-chelating' refers to the ability of such a functional group to strongly coordinate to cations contained in the surface of the sensing device, preferentially metal cations such as Ti(IV), Zr(IV), Hf(IV), V(V), Ta(V), Nb(V), Hf(V), Cr(III), Cr(VI), Mo(VI) or W(VI).

The amine groups in copolymers are the primary amines of lysine residues, but other groups can be used. For example, the polymer can be prepared using arginine or histidine, resulting in guanidino or imidazoyl cationic groups, respectively. Likewise, more than one PEG group can be provided, for example, by using as a starting material a small molecule with at least two carboxyl groups and at least two amino groups, for example, the dipeptide Glu-Lys.

For all embodiments, the molecular weight and number of PEG blocks per lysine block is determined such that the resulting copolymer has the properties of both the PLL and the PEG. If the proportion of PEG is too high, the adhesion of the polymer to the analytical or sensing substrate (chip) is reduced. If the proportion of PLL is too high, the ability of the PEG to reduce the non-specific adsorption of ions and molecules out of the analyte is insufficient. The polymers must have sufficient PEG character to minimize molecular interaction with the analytical or sensor chip. Polymers with too few PEGs per PLL are less suitable for minimizing these interactions. The polymers must also have sufficient PLL character to adequately bind to a chip surface. Polymers with insufficient PLL character fail to bind adequately. The polycationic polymer can be any polycation that provides a sufficient amount and density of cationic charges to be effective at adhering to the analytical or sensing substrate.

C. PEG/polyionic polymer dendrimers.

The PEG/poly(amino acid) dendrimers are copolymers where one or more linear PEG polymeric blocks are covalently linked to the focal point of a cationic dendrimer, for example, dendrimerically polymerized polylysine, such that the dendrimer fans out from the PEG. Preferably, the PEG is linked to the central point of the dendrimer, which is grown from the PEG as described in detail below. The particular utility of the dendritic construction is the ability to precisely control the mass of the resulting copolymer, the geometrical relationship between the polymeric blocks, and the degree of substitution. For instance, in the examples shown, there is exactly one PEG for a defined number of positive charges. In contrast, grafting preformed PEG molecules onto a polycationic backbone normally results in a random positioning of the PEG groups on the backbone.

The dendrimer preferably contains between 16 and 128 reactive amine groups, which correlates to a dendrimer of between generation 4 and generation 7. The molecular weight of the PEG is between 500 and 2,000,000, preferably between 5,000 and 100,000.

The dendrimeric PLL allows the formation of a compact structure, with a high charge density. These PEG-lysine dendrons are effective in preventing cell spreading when adsorbed on a simple anionic surface if the polymer contains about 8 or more positive charges (generation-3 dendron).

Other non-lysine-based dendrimers can also be prepared and are intended to be within the scope of the PEG/PLL dendrimers described herein. For example, the dendrimers can include polycationic groups other than amines, for example, quaternary ammonium salts. Further, synthetic, non-amino acid based cations can be included. Cationic amino acids such as ornithine can also be incorporated into the dendrimers.

D. Analyte-specific Ligands

The first requirement for an analytical or sensing device, which allows specific detection or recognition, is the resistance of the device surface towards non-specific adsorption. This requirement can be fulfilled by the copolymers described above, as well as in Example 1. The second requirement is the introduction of functional groups (called ligands) that allow specific interaction with select components of the analyte. Such ligands can be introduced into the PEG-grafted polyionic polymer. Preferentially such ligands are introduced at the free end of the PEG chain. The type of ligand is chosen according to the needs of the analytical or sensing task. Examples are:

Ligands that induce physico-chemical adsorption of a molecule as recognition unit for the subsequent analytical or sensing detection. Examples of the recognition unit are monoclonal or polyclonal antibodies, that will specifically bind complex molecules to be analyzed during the sensing step (called target molecules) such as peptides, proteins, oligonucleotides, DNA or RNA (fragments). The interaction of the recognition unit and the sensing device surface will be through electrostatic and/or van der Waals forces. Examples for the ligands are hydrophobic moieties such as methyl or trifluoromethyl groups, positively charged groups such as amines (carrying a positive charge below pH of 9), a quaternary amine (positively charged across the whole pH range), or negatively charged ligands such as carboxylate (negatively charged above pH 4).

Ligands that are able to bind covalently to functional groups of the recognition unit. Examples are ester, maleimide, succinimidyl, vinylsulfone, conjugated C=C double bonds, epoxy, aldehyde, ketone, silane or siloxane functionalities. These ligands can react with functional groups of the recognition unit, in particular with accessible amine, hydroxy or thiol groups.

Ligands that are able to bind to receptors on the surfaces of cells. In the approach of the immediately preceding paragraph, a recognition unit may be bound to the ligand directly, by reaction. An example is the reaction of a cysteine-containing peptide to a vinylsulfone ligand. Specific reaction between the thiol on the cysteine residue and the vinylsulfone ligand then results in immobilization of the peptide to the substrate, or to the polymer that is then adsorbed to the substrate. This coupling may be done with the polymer still in free solution, and thus the ligand definitionally becomes the peptide, or it may be done after the polymer with the cysteine-reactive ligand is adsorbed upon the substrate. Both approaches have advantages. In the first case, of the coupling of the peptide ligand to the polymer before adsorption to the substrate, the material may be more readily characterized. In the latter case, of coupling of the peptide ligand after adsorption of the polymer upon the substrate, the separation of the non-coupled peptide is very easy, being reduced to the process of rinsing. The case of the peptide ligand binding to receptors on the surface of a cell can be particularly interesting, e.g. in analysis of cellular behavior or in the therapeutic manipulation of cell behavior in a culture system or upon an implant.

Ligands that are able to bind specifically to a bioactive recognition moiety. Examples of such recognition units include antibodies in general, antigens, proteins, enzymes, oligonucleotides, c-DNA fragments and other groups or molecules provided they are able to interact specifically with the analyte in the subsequent analytical or sensing assay. These surface-attached recognition units must possesses further specific interaction sites, which can be used for specific recognition and binding of a particular analyte molecule. An example is the use of a polycationic PLL-g-PEG, where a fraction of the PEG chains are functionalized at the terminal position of the PEG chain with biotin. The functionalized PLL-g-PEG-biotin is adsorbed onto an analytical or sensing device surface, followed by the adsorption of streptavidin onto the biotin sites. Such a sensing surface is able to recognize and bind specifically biotinylated target molecules during the analytical or sensing assay. Alternatively, the adsorbed, biotinylated PEG-grafted polyionic copolymer can directly react with analytes that are streptavidin-conjugated. Details are given in Example 2.

Ligands that are able to interact with an intermediate reactive bifunctional molecule (called crosslinker). Firstly, one end of the homo- or (preferentially) hetero-functional cross linker is attached to the ligand of the copolymer. In a second step the other (free) end of the crosslinker is reacted with the recognition unit.

Ligands that are able to form stable complexes with a cation. In a second step the cation will form a complex either with the recognition unit directly through a suitable functionality or alternatively with a bifunctional crosslinker (in the latter case followed by procedure 4). Examples for the ligand include carboxylate, amide, phosphate, phosphonate, nitrilo triacetic acid and other known groups that are able to chelate cations. Examples for the cations include Mg(II), Ti(IV), Co(III), Co(VI), Cu(II), Zn(II), Zr(IV), Hf(IV), V(V), Nb(V), Ta(V), Cr(III), Cr(VI), Mo(VI) and other cations known to form stable complexes with chelating ligands.

Examples of suitable recognition units include antibodies in general, proteins, enzymes, lectins, oligonucleotides, c-DNA fragments and other groups or molecules provided they are able to interact specifically with the analyte in the subsequent analytical or sensing assay. Many interesting ligands in the bioanalysis of cellular responses are peptides. In such cases, the peptides may be coupled to the multifunctional polymers, e.g. to the termini of the polymer chains that are used to resist nonspecific adsorption, either before or after the polymer is adsorbed to the substrate. The peptide may be bound to the multifunctional polymer through a number of means, including reaction to a cysteine residue incorporated within the peptide. Cysteine residues are rarely involved in cell adhesion directly. As such, few cell adhesion peptides comprise a cysteine residue, and thus a cysteine residue that is incorporated for the purpose of coupling of the peptide will be the unique cysteine residue for coupling. While other approaches are possible, the preferred method is coupling of the peptide to the multifunctional polymer through a cysteine residue on the polymer. Other bioactive features can also be incorporated, e.g. adhesion proteins, growth factor proteins, cytokine proteins, chemokine proteins, and the like. Functionalized surfaces can be used in bioanalytical systems involving cells, in which some affecter of cell function is the measured feature. A test fluid may contain an analyte, to which the response of cells is sought. The cellular response may be used in as a measure of the presence or the activity of the analyte. Alternatively, the cellular response per se may be the knowledge that is sought, e.g. the migration response of a particular cell type to a growth factor, when the cells are migrating upon a particular adhesive substrate. The collection of such scientific information is of significant value in the screening of the activity of drug candidates, particularly when higher order cellular responses such as adhesion, migration, and cell-cell interactions are targeted.

Functionalized surfaces can be used in therapeutic systems involving cells, in which cells are cultured for later therapeutic use. In current therapeutic systems, cultured cells are sometimes used. Examples are in the culture of chondrocytes for transplantation in articular cartilage defects in the knee or in the culture of endothelial cells for transplantation in vascular grafts. In such cases, modulation and manipulation of the phenotype of the cells is of prime interest. For example, it may sometimes be of interest to stimulate cells into one phenotype (such as a proliferative phenotype), and later to stimulate them into a second phenotype (such as a differentiated phenotype). Alternatively, it may be desirable to maintain them in one particular phenotype, e.g. to maintain chondrocytes in a chondrocyte phenotype, rather than have them dedifferentiate into cells that more closely resemble fibroblasts. Surfaces and substrates may be useful in this. It is known that extracellular matrix interactions play an important role in regulating cell phenotype, and such interactions may be readily modified through the use of the multifunctional polymers of this invention. Functionalzed surfaces can be used in therapeutic systems involving cells, in which the cells are cultured and used in contact with the surface. As an example of this situation, bioreactors are used in some extracorporal therapeutic systems, such as cultured hepatocytes used to detoxify blood in acute hepatic failure patients. In such cases, one wants to maintain the hepatocytes in the reactor in a functional, differentiated state. The adhesive interactions between the cells and their substrate are thought to play an important role in these interactions, and thus the technology of this invention provides a means by which to control these responses.

Functionalized surfaces can be used in therapeutic systems involving cells, in which the functionalized surfaces is a component of an implant. The interactions between cells in an implant environment and the surface of an implant may play a controlling role in determining the biocompatibility of an implant. For example, on the surface of a stent implanted within the coronary artery, the presence of blood platelets is not desirable and may lead to in-stent restenosis. As such, it would be desirable to prevent the attachment of blood platelets to the stent surface. The attachment of all cells is not necessarily bad, however. For example, endothelial cells are thought to play a very positive role in preventing restenosis. As such, it would be desirable to treat the stent substrate with a functional coating that would prevent the nonspecific adsorption of proteins and also presents adhesion ligands that are capable of binding to endothelial cells but not blood platelets. The peptide REDV, based on an alternatively spliced domain in fibronectin, provides one potential such target, in that it has been reported that this sequence does not bind to receptors present on the blood platelet but does bind to receptors that are present on the endothelial cell (J. Biol. Chem 1992, 267 p.14019–26).

D. Surfaces or Substrates ("chips")

The type of substrates and surfaces of the analytical or sensing device suitable for the envisioned use depends on both the type of application, the type of analytical or sensing technique used, as well as on the suitability for binding the polyionic copolymer.

All types of substrates or substrate surfaces that are used in the area of analytical or sensing tasks which can be combined with any technique for the detection of the target molecules or analytes.

Suitable substrates or surfaces which include metals, metal oxides and/or polymeric materials are also discussed below in conjunction with the section on detection of analyte binding. Other substrates or surfaces include tissue and cell culture substrates, and means for immunoassay, which are typically formed of a polymer such as polystyrene or polycarbonate. Other supports or substrates include medical devices or prosthetics which are formed of metals (such as stainless steel), nylon, degradable and non-degradable biocompatible polymers such as poly(lactic acid-co-glycolide). Examples include bone implants and prosthetics, vascular grafts, pins, screws, and rivits. The most common substrate material for a stent is a metal. In many such implants, used in dentistry and in orthopedic surgery, metal implants are used. In other cases, polymeric implants may be more useful. It is possible to adsorb the multifunctional polymer to either polymeric or inorganic substrates, depending only upon the surface charge of the substrate.

Substrate and surface functionalization for use in other analytical assay platforms is also an important application of the technology. One of the largest areas in bioanalytical assays is the use of enzyme linked immunosorbent assays (ELISA) or linked immunosorbent assays (LISA). In these applications, a binding or recognition element is bound typically to a multiwell plate and then blocked with a protein based molecule to occupy surface area not containing the recognition element. The derivatized surface is then exposed to a solution containing analyte. The surface is then exposed to a second recognition element that is tagged with a molecule that can be assayed via any of the conventional spectroscopic or other methods. The above description is for a typical "sandwich" type assay, and this basic format can be modified in a variety of standard ways. For example, an antigen can be directly coupled to a surface and used to assay the level of antibody produced from immunological response to the antigen and present in biological fluids or tissues. This is a common technique used for determination of human disease or illness or even for determination of biocompatability of a drug or implant in which the degree of antibody production is measured as a function of drug level or dose.

One of the key issues with the assays is the blocking step that prevents non-specific binding. This step is time consuming and variable, and can generate false positive. Conventional methods for blocking of sites not occupied by the antigen or antibody include blocking with proteins, for example bovine serum albumin (BSA).

Functionalization of substrates and substrate surfaces for the analysis and control of cellular interactions in an important use, having application in culture-based assays, in therapeutics based on cell and tissue culture and bioreactors, and based on implants. Functionalized surfaces can be used in bioanalytical systems involving cells, in which the cellular response is the measured feature. In the field of cell biology, the response of a cell to a substrate is an important issue, and analysis of this response is an important bioanalytical task. For example, the response of a cell to extracellular matrix components is an important issue in cell adhesion and migration and is important in issues such as cancer metastasis and wound healing. As such, bioanalytical systems, including as a key component of them bioanalytical surfaces and substrates, are useful in measurement of such responses. Useful substrates are polymeric or inorganic. Modified polystyrene is a common cell culture substrate, modified so as to render the polystyrene anionic. Such as substrate alone has limited usefulness in bioanalysis of cellular behavior. It supports cell adhesion via proteins that spontaneously adsorb or are adsorbed from purified solutions. These proteins are subject to remodeling by cellular activities. As such, technology that would provide a well defined culture substrate would indeed be useful. In such usefulness, qualities such as the ability to resist nonspecific adsorption, to present biospecific adhesion ligands, and to remain stably adsorbed during extensive periods of culture.

II. Synthesis of Polyionic Copolymers Grafted with Non-Interactive Polymers and Analyte Specific Ligands.

A. Synthesis of Graft Copolymers.

PEG may be bonded to the α-amines of lysine residues of poly(L-lysine) as follows. Poly(L-lysine) (PLL) can be reacted with a PEG with one end protected (i.e., a protected monomethoxy PEG), the terminal hydroxyl of which has been previously activated with carbonyldiimidazole (CDI). The PLL and the activated PEG can be mixed in an aqueous solution buffered at pH 9 and allowed to react for 48 hours at room temperature. The number of PEG chains grafted per PLL chain may be controlled by adjusting the ratio of moles of activated PEG added per mole of added PLL. The reaction may not proceed to completion, i.e., the mole ratio of PEG to PLL in the reaction mixture may not be identical to that in the PEG-g-PLL product, but higher ratios of PEG to PLL will produce higher amounts of PEG in the PEG-g-PLL product.

The cationic domains tend to be highly reactive, and efforts must be made to control the extent of addition of PEG to PLL. Executing the reaction in the absence of water reduces deactivation of PEG and allows better stoichiometric control. For example, unprotected poly-L-lysine can be dissolved in water, then added to dimethylformamide (DMF) to make a solution that is 5% aqueous. The poly-L-lysine can then be reacted with CDI mono-activated PEG in stoichiometric amounts, followed by evaporation of solvent under vacuum yielding a PEG/PLL copolymer. Alternatively, unprotected poly-L-lysine can be dissolved in water and precipitated by adding NaOH. The precipitated polymer can then be added to anhydrous DMF and then reacted with CDI mono-activated PEG in stoichiometric amounts, yielding an $(A)x-b-(B)y$ copolymer. When the reaction is performed in the absence of water, side reactions involving the activated group can be reduced (i.e., deactivation is reduced), and at long reaction times the ratio of mole PLL to PEG in the polymer product more closely resembles than in the reactant mixture.

Solution polymerization of PLL may be carried out using monomers containing different epsilon protecting groups, which allows strict control over the degree of substitution of PEG onto PLL. N-carboxy anhydrides of various amino acids may be synthesized and polymerized into copolymers, as in the following example. N,N'-dicarbobenzoxy-L-lysine (Z,Z-lysine) can be reacted with phosphorus pentachloride to yield α,N-carbobenzoxy-α,N-carboxy-L-lysine anhydride. α,N-carbobenzoxy-α,N-tert-butyloxycarbonyl-L-lysine (Z,boc-lysine) can be reacted with sodium methoxide to yield the sodium salt of Z,boc-lysine. The sodium salt of Z,boc-lysine can be reacted with phosphorus pentachloride to yield α,N-tert-butyloxycarbonyl-α,N-carboxy-L-lysine anhydride. Z,Z-lysine anhydride can be added to Z,boc-lysine anhydride, and the two monomers can be polymerized by the addition of sodium methoxide as an initiator. A copolymer results, poly(αboc-lysine)-co-(αZ-lysine). The boc groups can be removed by addition of the polymer to trifluoroacetic acid for fifteen minutes.

The salt form can be converted to the free base by reaction with a reactant such as pyridine. The free amines on the polymer can then be reacted with CDI PEG in DMF. The Z groups can then be deprotected by adding the polymer to HBr in acetic acid for fifteen minutes, yielding an (PEG)x-b-(PLL)y copolymer, where the ratio of PEG to PLL in the final product can be controlled by the initial ratio of boc protected lysines.

It may be desirable to produce versions of the polymer that are not of a brush structure. This may be facilitated by not deprotecting the epsilon amines of PLL, so that the only reactive groups are the amine and carboxyl termini. For example, reaction of CDI activated PEG with poly α,N-carbobenzoxy-L-lysine in DMF yields an (A)x-(B)y copolymer. Activation of the carboxyl terminus of the (A)x-(B)y copolymer with TSU followed by reaction with mono-amino PEG in DMF yields an (A)x-(B)y-(A)z copolymer.

B. Synthesis of Functionalized Graft Copolymers.

The synthesis of PEG-grafted polyionic copolymers, for which all or part of the PEG side chains are functionalized with a particular group at the terminal or close to terminal position, follows the same procedures as outlined above. However, instead of using a one end protected PEG (e.g. methoxy terminated PEG), a functionalized PEG is used. Either only functionalized PEG is used or (preferentially) a mixture of functionalized and non-functionalized PEG. The functional group at the end of the PEG chain are chosen according to the needs and concept of the analytical assay. The ratio of functionalized PEG to non-functionalized PEG depends again on the requirements of the analytical or sensor assay. It has to be optimized for a given type of application. An example of the optimization of this ratio is given in Example 2.

The details of a particular synthesis are given in Example 2 for the case of biotinylated PEG/PLL to be used in PEG-biotin-streptavidin-biotinylated type of assay. An alternative but related approach is provided in Example 3.

Non-charged, hydrophilic side chains other than PEG can be used as long as they impart the property of non-interactiveness or adsorption resistance to the treated surface III. Methods for Surface Modification with Graft Copolymer.

A. Methods for modifying Chip Surfaces or Substrates

Six typical general protocols for the modification of a chip surface intended to be used for bioaffinity sensing using the optical waveguide technique with or without fluorescence detection are described.

Protocol A

1) Pretreatment of the chip surface comprising a glass slide on which a metal oxide layer as waveguiding layer has been deposited: a) ultrasonic cleaning in an organic solvent; b) plasma treatment of the surface in an oxygen atmosphere
2) Spontaneous adsorption of a monolayer of the cationic PLL-g-(PEG)$_x$(PEG-biotin)$_{1-x}$ out of an aqueous solution. 1-x denotes the fraction of functionalized PEG chains in comparison to the total number of PEG chains.
3) Rinse
4) Exposure of the chip surface with an aqueous solution of streptavidin, binding specifically to the surface accessible biotin ligands.
5) Rinse of the surface to remove loosely (non-specifically) bound streptavidin.
6) Specific adsorption of an analyte solution containing biotin-conjugated target molecules to the surface-immobilized streptavidin sites.
7) Rinsing of the surface to remove weakly bound (non-specifically adsorbed) molecules.
8) Detection of the specifically bound target molecule using the optical waveguide technique. This is accomplished by e.g. varying the incoupling angle until the conditions for incoupling are met. The determination of the effective index through measurement of the electric and magnetic mode ($T_E$ and $T_M$) then allows determining quantitatively the mass of the (specifically) adsorbed biotin-conjugated target molecule.

Alternatively to 8), the biotin-conjugated recognition molecule (antibody) is adsorbed to the streptavidin-functionalized chip surface. The target molecule is specifically immobilized at the chip surface, followed by reaction with a tracer molecule (fluorescently labeled antibody to the target molecule). The evanescent field generated at the surface of the waveguide is then used to excite fluorescence of the tracer molecule. The fluorescence is detected using a fluorescence detector situated on the side opposite to the liquid flow cell, making use of the very high detection sensitivity of the fluorescence technique in combination with the advantage that practically only the labeled molecules attached to the surface are fluorescence-excited, with minimal contribution from 'bulk' fluorescence.

Protocol B

1) Pretreatment of the chip surface comprising a glass slide on which a metal oxide layer has been deposited, as a waveguiding layer: a) ultrasonic cleaning in an organic solvent; b) plasma treatment of the surface in an oxygen atmosphere
2) Spontaneous adsorption of a monolayer of the cationic PLL-g-(PEG)$_x$(PEG-vinylsulfone)$_{1-x}$ out of an aqueous solution. 1-x denotes the fraction of functionalized PEG chains in comparison to the total number of PEG chains
3) Attachment of single stranded c-DNA fragments containing a thiol group that adds to the vinylsulfone function via a nucleophilic additions.
4) Rinse of the surface to remove weakly bound (not covalently linked) c-DNA.
5) Specific adsorption of the complimentary DNA strand (target molecule) that has been previously labeled with a fluorescence tag to the c-DNA recognition ligand.
6) Rinse to remove weakly bound (non-specifically attached) molecules. Detection of the specifically bound DNA fragments upon determination of the intensity of the fluorescence excited in the evanescent field of the waveguide.

Protocol C

1) Cleaning of a gold-coated chip using organic solvents.
2) Self-assembly of an co-amino-terminated alkanethiol out of alcoholic solution to form an ordered self-assembled monolayer (SAM) through interaction of the thiol group with the gold substrate. This SAM will acquire positive charges when in contact with an aqueous environment at pH below 9 (e.g. at neutral pH) as a consequence of the terminal amino groups being partly protonated.
3) Spontaneous adsorption of the polyanionic (negatively charged) polymer poly(glutamic acid)-g-(PEG)$_x$(PEG-succinimid)$_{1-x}$ onto the positively charged Au-SAM.
4) Reaction of the succinimid groups accessible at the surface of the polymer-adsorbed chip with a primary amine group of an antigen.
5) Rinse to remove loosely bound (non-specifically adsorbed) antigen. Specific reaction of the surface-bound antigen with the corresponding antibody in the analyte solution monitored in situ by the Surface Plasmon Resonance (SPR) technique.

Protocol D

1) Pretreatment of the chip surface comprising a glass slide on which a metal oxide layer has been deposited as a waveguiding layer: a) ultrasonic cleaning in an organic solvent; b) plasma treatment of the surface in an oxygen atmosphere.
2) Microfluid patterning of the waveguide chip surface with an aqueous solution of PLL-g-PEG using a polymer stamp with a micron-sized pattern at the stamp surface. This process produces a patterned (e.g. a type of line pattern)

surface consisting of regions that have been PLL-g-PEG treated (along the microfluidic channel network) and regions that have not been treated (where the stamp protected the surface).

3) Treatment of the patterned waveguide chip surface in an aqueous solution of the cationic PLL-g-$(PEG)_x(PEG$-vinylsulfone$)_{1-x}$. This step will fill the uncovered regions in step 2) with the functionalized PLL-g-$(PEG)_x(PEG$-vinylsulfone$)_{1-x}$, producing a pattern with non-functionalized and functionalized PLL-g-PEG.

4) Rinse

5) Adsorption or attachment of different recognition molecules in different regions with adsorbed functionalized PLL-g-PEG using techniques that allow localized recognition molecules deposition such as ink-jet techniques, printing or fluidic patterning.

6) Rinse

Application of a solution containing multiple fluorescently labeled analytes and two-dimensionally resolved, parallel detection of the specific binding of different analyte molecules at spatially separated, different recognition sites by 2-dimensionally resolved detection of the fluorescence excited by the evanescent field of the optical waveguide.

Protocol E

1) Pretreatment of the chip surface comprising a glass slide on which a metal oxide layer has been deposited as a waveguiding layer: a) ultrasonic cleaning in an organic solvent; b) plasma treatment of the surface in an oxygen atmosphere 2) Spontaneous adsorption of a monolayer of PLL-g-$(PEG)_x(PEG$-R'-$OPO_3)_{1-x}$ out of an aqueous solution. 1−x denotes the fraction of functionalized PEG chains in comparison to the total number of PEG chains. R' is a crosslinker used to attach the phosphate group at the terminal position of the PEG chain in the course of the synthesis of the modified PEG-g-PLL.

3) Rinse

4) Exposure of the chip surface with an aqueous solution of a soluble zirconium Zr(IV) salt such as zirconium (IV) nitrate. Zirconium (IV) cations will bind to the surface accessible phosphate groups of the modified PEG-g-PLL polymer.

5) Rinse of the surface to remove loosely bound, not phosphate-coordinated Zirconium (IV) cations 6) Specific adsorption of phosphate or phosphonate-conjugated antibody molecules to the zirconium (IV) sites. The phosphate or phosphonate group of the antibody will coordinatively attach to the immobilized zirconium(IV) cations via formation of a complex.

7) Rinsing of the surface to remove weakly bound (non-specifically adsorbed) molecules.

8) Exposure of the functionalized chip to a solution that contains an unknown mixture of different proteins. Detection of the protein molecules that interact specifically with the surface accessible, immobilized antibodies on the chip surface upon determination of the intensity of the fluorescence excited in the evanescent field of the waveguide.

Protocol F

1) Pretreatment of the chip surface comprising a suitable substrate such as silicon on which an electronic circuit suitable for the use as a nerve cell-based sensor has been produced.

2) Microfluidic patterning of the chip surface with an aqueous solution of PLL-g-PEG using a polymer stamp with a micron-sized pattern at the stamp surface that is compatible with the electric network of the sensor surface. This process produces a surface consisting of regions that have been PLL-g-PEG treated (along the microfluidic channel network) and regions that have not been treated (where the stamp protected the surface).

3) Treatment of the patterned chip surface in an aqueous solution of the cationic PLL-g-$(PEG)_x(PEG$-peptide$)_{1-x}$. This step will fill the uncovered regions in step 2) with the functionalized PLL-g-$(PEG)_x(PEG$-peptide$)_{1-x}$, producing a pattern with non-functionalized and functionalized PLL-g-PEG. The oligopeptide is e.g. YIGSR known to be a specific sequence in the protein laminin that induces the attachment and migration of nerve cells.

4) Exposure of the patterned surface to a cell-culture solution containing nerve cells. Attachment and spreading of the nerve cells in the protein- and cell-adhesive areas.

Use of the living-cell-based sensor for sensing (via monitoring the electrical signals of the attached nerve cells) environmentally relevant compounds such as gaseous or liquid components that are toxic to nerve cells or unknown components in order to test their potential toxicity.

B. General Protocols for the Preparation and Use of Non-Chip Substrates

The substrates can be modified in a variety of ways. Non-modified and modified copolymers can be adsorbed onto suitable surfaces either in pure form or as mixtures. The optimum choice depends on the type and concentration of the ligand molecules, the targeted receptor, and the substrate properties. Examples of substrates to which the copolymer can be applied include bioanalytical devices such as ELISA or LISA plates, lateral flow assay substrates such as nitrocellulose, nylon, or PVDF membranes, polymeric microparticles or inorganic particles, capillaries for electrophoresis, fiber optics, or "lab on a chip" devices.

The materials described herein are particularly suited for these applications in that the polyionic copolymers allow easy and efficient post production modification of the suface, tailored to the desired application, with non-interactive properties and of specific interaction properties. The adsorbing domain of the multifunctional polymer should have opposite charge as that of the substrate prior to adsorption of the polymer, leading to stable and strong adsorption. The considerations for the domains of the copolymer that resist nonspecific adsorption are also similar to those described above. Nonionic water-soluble polymers such as poly (ethylene glycol) are especially preferred. On the termini of these chains may be placed either reactive groups or directly binding groups, to provide for attachment device surfaces. Alternatively, no biological recognition element may be used, leading to a surface that resists nonspecific attachment but does not promote biospecific attachment, or the surface may be pretreated with a reactive moiety and the free surface area that is not derivitized with the reactive moiety subsequently can be "filled in" with either the polymer with no biologicial element that resists nonspecific attachment, or alternatively, with a second protocol.

From the viewpoint of the surface treatment, there are two basic methods:

1) In a type of batch process where the surface is functionalized. In a fluid manifold, one or several analytes and reagents are locally applied to the surface. After awaiting the completion or near completion of the bioaffinity reaction (incubation step), the surface is washed in a buffer.

2) In a continuous process where the surface to be functionalized is part of a gaseous or liquid cell or flow-through system. The conditioning of the surface can be done in a continuous and continuously monitored process within that liquid or flow-through cell, followed by in situ monitoring of the signal due to the specific interaction and adsorption or attachment of the specific target molecule in the analyte solution. The original surface may afterwards be restored/regenerated again and conditioned for the immediately following next bioaffinity assay. This may be repeated many times.

B. General protocols for the modification of a surface intended to be used for bioanalytical devices other than for screening and detection.

Protocol A

1) Pretreatment of the surface to generate charged surfaced if not inherent to material as obtained.
2) Spontaneous adsorption of a monolayer of the cationic PLL-g-(PEG)$_x$(PEG-Y)$_{1-x}$ out of an aqueous solution. 1−x denotes the fraction of PEG chains functionalized by reactive molecule Y in comparison to the total number of PEG chains.
3) Rinse
4) Exposure of the surface with an aqueous solution of reactive molecule, binding specifically to the surface ligands.
5) Rinse of the surface to remove loosely (non-specifically) bound reactive molecule.

Subsequent methodology according to standard protocol for the analytical technique.

Protocol B

1) Pretreatment of the surface to generate charged surface if not inherent to material as obtained.
2) Reaction of the cationic PLL-g-(PEG)$_x$(PEG-Y)$_{1-x}$, in solution with ligand reactive with molecule Y. 1−x denotes the fraction of PEG chains functionalized with molecule Y in comparison to the total number of PEG chains.
3) Spontaneous adsorption of a monolayer of the derivatized cationic PLL-g-(PEG)$_x$(PEG-ligand)$_{1-x}$ out of an aqueous solution.
4) Rinse
5) Subsequent methodology according to standard protocol for the analytical technique.

Protocol C

1) Pretreatment of the surface to generate charged surface if not inherent to material as obtained.
2) Spontaneous adsorption of a monolayer of the derivatized cationic PLL-g-(PEG) out of an aqueous solution.
3) Rinse
4) Subsequent methodology according to standard protocol for the analytical technique.

Protocol D

1) Treatment of the surface with reactive moiety of interest.
2) Rinse
3) Spontaneous adsorption of a monolayer of the derivatized or non-derivatized cationic PLL-g-(PEG) out of an aqueous solution. (as per Protocol A, B, or C)
4) Rinse
5) Subsequent methodology according to standard protocol for the analytical technique.

Examples of various applications of these materials and techniques are provided.

Polystyrene, used for example as microwell plates, can be rendered negatively charged at physiological pH. This material generally supports the adsorption of a wide variety of proteins solution for assay. Microwell plates can be purchased commercially with negatively charged surfaces.

The negatively charged 96 microwell plate is exposed to PLL-g-(PEG)$_x$(PEG-VS)$_{1-x}$ where VS denotes a vinylsulfone functionality, and coupled to IgG or IgG fragment as in Protocol A. The amount of IgG thus displayed in the microwell may be controlled readily through the quantity x, x=0 leading to a large amount of exposed IgG and the quantity x=1 leading to no exposed ligand. The amount of antigen contained in a solution may then be analyzed via conventional ELISA methods. For example, subsequent steps for a standard "sandwich" assay would be incubation of the IgG derivatized microwell plate to the antigen solution for 2 hours to overnight, rinsing three times with PBS or other buffer solution, incubation with a horseradish peroxidase labeled IgG, rinsing with buffer again to remove non-specifically bound HRP labeled IgG, and then detection of bound antigen through a peroxidase generated adsorbing precipitate.

The amount of IgG may also be readily varied by adding stoichiometrically limited amounts of the IgG, and then passivating the other reactive groups if desired by exposure to cysteine or beta mercaptoethanol.

The amount of IgG may also be readily varied by adding the ligand simultaneously with another reactant, such as cysteine or beta mercaptoethanol. The fraction of the VS groups that react with the IgG will be determined by the molar ratios of the two agents and the relative reactivities of the two agents.

Two or more biorecognition elements may be added to the VS sites, either in parallel or in series.

Of importance is that the PEG component of the coating acts as a pre-applied blocking agent, eliminating the need for subsequent blocking steps normally required for microwell plate or other analytical type methods. This is significant in that it can reduce the time required for the assay by many hours and reduces uncertainty in assay performance which arises from incomplete or variable blocking often observed using conventional blocking agents such as bovine serum albumin.

It is also possible to adsorb the biorecognition element directly to the microwell plate surface, and then subsequently coat the free surface area with a derivatized or underivatized PLL-g-PEG following Protocol A or B or D. Alternatively, if the biorecognition element is not active in the attached form, it can be derivatized with a peptide or other tag that will allow reaction with the reactive ligand of the derivatized PLL-g-PEG. For example, a thiol containing tag will react with the vinylsulfone group of (PEG)$_x$(PEG-VS)$_{1-x}$. The ability to control the binding site of the antigen or antibody can confer higher surface activity.

In another example, lateral flow assay substrates which are commonly formed of nylon 6,6 are modified with the graft copolymer. As with other bioanalytical assays, it is of considerable interest to limit nonspecific adsorption to the membrane surface. One use of lateral flow assays is for determination of antibody concentrations in a biological solution which are produced in response to exposure to an antigen. Nylon 6,6 is purchased commercially with a negatively charged surface that is stable from pH 3 to 10. The surface is then exposed in the detection region to PLL-g-(PEG)$_x$(PEG-VS)$_{1-x}$ and rinsed. The remaining material is then exposed as appropriate to PLL-g-PEG with no reactive group to block adsorption to areas outside the detection region and any uncoated regions within the detection region. The PLL-g-(PEG)$_x$(PEG-VS)$_{1-x}$ in the detection region is then coupled to an antigen, as in Protocol A. Assay for an antibody to this antigen is performed by flowing a solution to be analyzed through the substrate which results in attachment of the antibody to the bound antigen. The amount of bound antibody/antigen complex is then determined by exposure of the complex to a labeled anti-IgG and quantitated spectroscopically.

Alternatively, the lateral flow assay surface could be coated with a pre-derivatized PLL-g-PEG as in Protocol B or derivatized with multiple antigens or antibodies. The amount of antigen or antibody present can be varied to optimize the coupling reaction and subsequent detection.

C. General Protocols for the Preparation and Use of Substrates for use in Cell-Based Systems The analytical or therapeutic surfaces and substrates may be formed by a number of ways and for a number of purposes, as described below. From the general perspective of the choice of multifunctional copolymers, the same principles hold as described above for chip-based devices. The adsorbing domain of the multifunctional polymer should have an opposite charge to that of the substrate prior to adsorption of the polymer, leading to stable and strong adsorption. The considerations for the domains of the copolymer that resist nonspecific adsorption are also similar as to those described above. Nonionic water-soluble polymers such as poly(ethylene glycol) are especially preferred. On the termini of these chains may be placed either reactive groups (as in Protocol A below) or directly binding groups (as in Protocol D below), to provide for attachment to cell surfaces. Alternatively, no biological recognition element may be used, leading to a surface that resists nonspecific attachment but does not promote biospecific attachment (as in Protocol C below).

Protocol A

Adsorption of multifunctional polymers onto bioanalytical or biomedical materials may be accomplished as follows.

1) Pretreatment of the polymer or metal surface comprising cleaning under conditions such that the native surface charge is displayed, e.g. the native surface charge at the operating pH of an underlying polymer layer or the surface charge of a metal oxide coating atop a metal substrate. Such cleaning may be accomplished by rinsing, by washing with a detergent and then rinsing to remove detergent, or, for stable materials such as metals, by cleaning in a reactive plasma. Some polymers may be pre-treated as well by plasma processing, especially to introduce surface charge. For example, so-called tissue culture polystyrene is often produced by processing polystyrene in an air or an oxygen plasma, which both cleans the substrate as well as introduces modifications into the surface that are negatively charged at neutral pH. Most metal surfaces, such as stainless steel, titanium and tantalum, are negatively charged at neutral pH, due to the characteristics of the metal oxide overlayer. For the remainder of this protocol, it is assumed that the substrate is negatively charged.

2) Spontaneous adsorption of a monolayer of the cationic PLL-g-(PEG)$_x$(PEG-VS)$_{1-x}$ out of aqueous solution. 1-x denotes the fraction of reactively functionalized PEG chains in comparison to the total number of PEG chains. VS denotes a vinylsulfone function, which will react with thiols at neutral or basic pH. A number of other reactive groups can be used, such as maleimides, acrylates and quinines—the only condition is that these groups must not be highly reactive with amines (e.g., on the lysine) at adsorption pH. Amine reactive groups can be used, however, if the positively charged sites on the backbone are substituted with a nonreactive group, such as would be obtained by the use of poly(arginine) rather than PLL.

3) Rinse

4) Exposure of the material surface to peptide comprising a cysteine residue in aqueous solution at a neutral or basic pH, e.g. from pH 7.5–9. The rate of reaction is dependent upon the pH of the solution, being more rapid at basic pH than at neutral pH.

5) Rinse

Protocol B

Adsorption of multifunctional polymers upon substrates that are positively charged, such as an amino-containing or amino-modified polymer or aluminum oxide upon aluminum, can be obtained exactly as described above, except by substituting an anionic polymer, such as polyglutamic acid or polyaspartic acid or polyacrylic acid for the PLL.

Protocol C

Adsorption of multifunctional polymers lacking a specific recognition element can also be used, when it is desired to simply block nonspecific interactions and not to promote specific interactions. This can be achieved exactly as obtained in Protocols A or B, using polymers where x=1.

Protocol D

The biological recognition element can be attached to the multifunctional polymer prior to adsorption to the substrate, as described below.

Adsorption of multifunctional polymers onto bioanalytical or biomedical materials may be accomplished as follows.

1) Pretreatment of the polymer or metal surface comprising cleaning under conditions such that the native surface charge is displayed, e.g. the native surface charge at the operating pH of an underlying polymer layer or the surface charge of a metal oxide coating atop a metal substrate. Such cleaning may be accomplished by rinsing, by washing with a detergent and then rinsing to remove detergent, or, for stable materials such as metals, by cleaning in a reactive plasma. Some polymers may be pre-treated as well by plasma processing, especially to introduce surface charge. For example, so-called tissue culture polystyrene is often produced by processing polystyrene in an air or an oxygen plasma, which both cleans the substrate as well as introduces modifications into the surface that are negatively charged at neutral pH. Most metal surfaces, such as stainless steel, titanium and tantalum, are negatively charged at neutral pH, due to the characteristics of the metal oxide overlayer. For the remainder of this protocol, it is assumed that the substrate is negatively charged.

2) Spontaneous adsorption of a monolayer of the cationic PLL-g-(PEG)$_x$(PEG-RE)$_{1-x}$ out of aqueous solution. 1-x denotes the fraction of functionalized PEG chains in comparison to the total number of PEG chains. RE denotes a recognition element function, such as a peptide or protein or saccharide or polysaccharide.

3) Rinse

These techniques are useful for example, with cell culture substrates, which are typically formed of polystyrene. The polystyrene is or can be surface modified so as to render it negatively charged at physiological pH. This material generally supports the adsorption of a wide variety of proteins from cell culture medium, including fibronectin and vitronectin from serum-containing medium, a situation which prevents the investigation of biospecific interactions between cells and their substrate.

Tissue culture polystyrene is exposed to PLL-g-(PEG)$_x$ (PEG-VS)$_{1-x}$ and coupled to the adhesion peptide GCGRGDSPK, as in Protocol A. The amount of peptide thus displayed upon the culture substrate may be controlled readily through the quantity x, x=0 leading to a large amount of exposed peptide and the quantity x=1 leading to no exposed peptide. Cell behavior on the bioanalytical substrate may be measured, e.g. adhesion, spreading, growth, migration, or higher order functional indicators, such as the production of growth factors, cytokines and chemokines, the expression of matrix proteins, and so forth.

The amount of grafted peptide may also be readily varied by adding stoichiometrically limited amounts of the peptide GCGRGDSPK, and then passivating the other reactive groups if desired by exposure to cysteine or beta mercaptoethanol.

The amount of grafted peptide may also be readily varied by adding the peptide GCGRGDSPK simultaneously with another reactant, such as cysteine or beta mercaptoethanol. The fraction of the VS groups that react with the peptide biorecognition element will be determined by the molar ratios of the two agents and the relative reactivities of the two agents.

Two or more biorecognition elements may be added to the VS sites, either in parallel or in series.

Nonpeptide biorecognition elements may also be added to the VS groups, e.g. thiol-containing sugars or polysaccharides. Proteins may readily be added to the VS groups, e.g. by exposure to a protein that contains one or more free cysteine residues.

In another example, the cell phenotype in therapeutic bioreactors can be manipulated by application of the graft copolymer to the cell culture substrate. The use of cells as therapeutic agents has been extensively explored. An example is the use of hepatocytes in extracorporal bioreactors as a liver support device in patients with liver failure. Problems in such approaches have been encountered in preventing the overgrowth of unwanted cell sub-populations and in maintaining the proper phenotype of the cells, both in this and other examples. This may be minimized as follows.

Anionic microcarrier beads are treated by exposure to PLL-g-$(PEG)_x(PEG-VS)_{1-x}$ and then grafting with a thiol-containing galactose moiety, as in Protocol A. Hepatocytes bind to galactose via the asialoglycoprotein receptor, which is absent on most other cells, such as fibroblasts that may be present in a clinical preparation of hepatocytes intended for therapeutic use in a bioreactor. It is also known that adhesion of hepatocytes to substrates via galactose binding to the asialoglycoprotein receptor can maintain the hepatocyte phenotype more effectively than, for example, adhesion to collagen.

Hepatocytes are seeded on the microcarriers and allowed to attach in a spinner flask as usual. The microcarriers are then placed in a bioreactor, e.g. within the shell space of a hollow fiber bioreactor, with human plasma perfused from the patient, via a blood cell separator, to remove toxins from the plasma.

In still another example, a coronary artery stent, formed from stainless steel, is exposed to PLL-g-PEG as in Protocol C, to block nonspecific protein adsorption and thus blood platelet adhesion upon the surface. The stent may be coated either prior to mounting on a deployment catheter or after, and it may be dried after the final rinse procedure or not. It may thus be coated either in a manufacturing facility or intraoperatively. The treated stent is deployed within the coronary artery as usual in the treatment of coronary artery disease.

A coronary artery stent, formed from stainless steel, is exposed to PLL-g-$(PEG)_x(PEG-VS)_{1-x}$ and then to the endothelial cell-specific peptide GCGREDVG, as in Protocol A. The treated stent is deployed in the coronary artery as usual. In this case, the PEG component serves to reduce the adsorption of plasma proteins, including fibrinogen, and the corresponding in-stent thrombosis and restenosis that may result therefrom. The biological recognition element GDGREDVG serves to promote the attachment and overgrowth of endothelial cells, to provide for a more natural biological covering of the stent surface after deployment and endothelial cell migration over the stent.

The stent may also be treated with the multifunctional polymer already grafted with the biological recognition element. A coronary artery stent, formed from stainless steel, is exposed to PLL-g-$(PEG)_x$ $(PEG-GCGREDVG)_{1-x}$, as in Protocol YYD, with x=0.75.

IV. Means for Detection and/or Quantitation of Analyte Binding.

A preferred technique is the use of optical waveguide techniques, where the evanescent field is able to sense the analyte that has specifically interacted with the recognition unit in the adsorbed layer of the functionalized PEG-grafted polyionic copolymer. The advantage of the technique is the fact that it only senses analyte molecules close to the surface (i.e. adsorbed or attached to the surface) and not the analyte molecules in the bulk of the solution to be analyzed. A second advantage is the high sensitivity of the technique, which is typically of the order of of the order of 1 ng/cm2 of adsorbed analyte for sensors based on changes of the effective refractive index (such as grating coupler sensors). The detection sensitivity can be further increased if fluorescently labeled target molecules are used and the fluorescence signal excited by the evanescent field is used. As a consequence, substrates, chips or devices are preferred which comprise an optical waveguide with an optically transparent waveguiding layer. "Optically transparent" in this context shall mean transparency at least at the wavelength of an adequate excitation light source and optionally of the fluorescence or more general luminescence generated by the excitation, typically in the visible or near infrared, for interrogation of the analyte molecules.

The optical waveguides can be designed as self-supporting single- or multilayer systems. Glass plates or glass or transparent polymeric fibers without cladding are examples of self-supporting single-layer systems. For purposes of enhanced sensitivity, however, substrates, chips or devices are preferred which comprise an optical thin film waveguide comprising a first optically transparent layer (a) deposited on a supporting second layer (b) with lower refractive index than layer (a). Especially in case of support materials (second layers (b)) which are only partially or non-transparent or are fluorescent themselves, it is preferred, if the substrates, chips or devices comprise another optically transparent layer (b') with lower refractive index than layer (a) and a thickness between 5 nm and 10000 nm, preferably between 10 nm and 1000 nm, which is located between layers (a) and (b) adjacent to layer (a).

In general, however, using optical waveguides with or without fluorescence detection, it is preferred that the substrates (layer (b)) are optically transparent, such as glass or transparent polymers, have to be used. Suitable waveguiding layers that are deposited onto the transparent substrate are high-refractive-index transparent materials. Examples include oxides of titanium, silicon, tantalum, niobium, hafnium, zirconium, or mixtures thereof. An additional possibility is to coat the waveguiding layer with an additional thin coating that is particularly suited to attach the polyionic polymer backbone. The only requirements are that this additional coating has to be transparent and thin enough not to adversely affect the optics of the waveguiding process. Other examples are metal nitrides, oxynitrides, carbides, or borides.

Such inorganic layers are generally deposited by physical or chemical vapor deposition or by wet-chemical techniques such as sol-gel techniques onto a suitable substrate such as glass or polymer. It is preferred that the substrates, chips or devices include one or more optical coupling elements for incoupling the excitation light into the optically transparent layer (a). These optical coupling elements can be selected form the group of prism couplers, evanescent couplers comprising joined optical waveguides with overlapping evanescent fields, end face couplers with focusing lenses, preferably cylindrical lenses, located adjacent to the waveguiding layer (a), and grating couplers. Preferred grating couplers are diffractive gratings selected from the group of relief gratings of any profile, such as rectangular, triangular or sinusoidal profile, and phase gratings or volume gratings with a periodical modulation of the refractive index in the optically transparent layer (a). For ease of production and its reproducibility, diffractive relief gratings with a rectangular profile are the most preferred optical coupling elements.

Most of the metal oxides (and other metal compounds) carry a positive or negative charge at or near to neutral pH. In particular, titanium oxide, tantalum oxide and niobium oxide, with isoelectric points (IEP) below 7, spontaneously acquire a negative charge in contact with aqueous environments at neutral pH and are therefore suitable to be used in combination with the polycationic polymers. Another possibility is to artificially impose a positive or negative charge onto the waveguiding surface, e.g. through introduction of functional groups such as carboxylate, sulfonate or phosphate or alternatively of positive charges through introduction of functional groups such as amines. There are a variety of techniques known that are suitable for such a pretreatment. Examples include silanization with amino-terminated silanes such as aminopropyltriethoxysilane (APTES) or other silanes carrying a positive or negative charge upon contact with an aqueous environment.

A further sensing technique is the surface plasmon resonance (SPR) technique, which uses an evanescent field generated in thin metal films. If this metal film spontaneously forms a passive oxide film or can be artificially oxidized, this oxide film with positive or negative charge in contact with an aqueous medium can again be used directly to attach polyionic polymers of the right charge. Since noble metal surfaces such as gold often used in SPR are generally not covered by an oxide film, the surface has first to be treated by chemical or electrochemical techniques in order to generate positive or negative charges. A preferred pretreatment technique is the use of self-assembled monolayers of alkane thiols well known to form ordered monolayers on gold and silver surfaces. If bifunctional thiols are used carrying a functional group in the co-position, which will acquire a positive or negative charge in contact with aqueous environments, such pretreated metal surfaces can again be used in combination with polyionic copolymers in the same or similar way as discussed above for the metal oxide surfaces with spontaneously formed charges. Examples include thiols with a terminal amino, quartenary ammonium, carboxylate or phosphate group.

Independent of the type of substrates and surfaces used, cleaning of the surface is an important aspect of this technology. Controlled surface cleanliness is necessary to ensure an optimum degree of adsorption or attachment of the polyionic copolymer to the positively or negatively charged device surface. In the case of the metal oxides discussed above, several cleaning procedures have been tested and optimized for the intended use of the polyionic copolymers in the analytical and sensing area. These include organic solvent cleaning, acid treatment, UV/ozone treatment, glow discharge, plasma cleaning and combinations (see Examples 1 and 2). Plasma cleaning can be done in an oxygen, water vapor, nitrogen or argon gas at reduced pressure. The cleaning of the oxide surface is important to reduce the natural hydrocarbon concentration and or to increase the number of available hydroxy groups at the oxide surface. The hydroxy groups are known to be essential in the formation of charges in contact with an aqueous environment. Plasma treatment in water vapor is preferred if the aim is to increase the number of hydroxyl groups at the surface.

Alternative excitation and detection methods are commonly known and include fluoescence excitation via direct interaction with an excitation source (not through evanescent field excitation), chemiluminescent, adsorption and radioisotope labeling. In all spectroscopic cases, the wavelength used is dependent on the absorbing or emitting molecule as well as the substrate, and can range for example from the near Infra-red to the visible region of the spectrum. Adsorption and fluorescence are commonly used in assays such as lateral flow assays, fiber optic based assays, or multiwell plate based assays in which either transmission or reflection mode are employed. In cellular assays, techniques include fluorescence based microscopy and two photon techniques.

V. Fabrication of Patterned Surfaces

Two-dimensionally patterned surfaces are an important aspect of modern analytical and sensor devices such as biochips used today or in the future in DNA, RNA or protein microarray and immunoassay technologies. The technique allows the parallel detection of many different target molecules in one analyte of complex composition through specific surface functionalization and recognition site immobilization on a local scale. The three basic prerequisites are a surface technology that allows one to reproducibly fabricate geometrically patterned surfaces, a technique to immobilize recognition units on a localized scale and detection techniques that are compatible with the local scale of the individual assay.

PEG-grafted, polyionic copolymers are suitable to fabricate patterned surfaces on a millimeter to micron scale. A preferred way is to use the established microfluid patterning technique. A typical application involves a polymeric stamp that has a three-dimensionally structured surface, e.g. a number of channels in one or in two directions. This stamp is brought in close contact with an analytical or sensor chip surface forming an array of channels between the stamp and the chip surface. The non-functionalized PEG-grafted polycationic copolymer solution is introduced into the stamp/chip fluidic channel network either by capillary forces or by a forced flow using a pump. After having adsorbed the polyionic copolymer A according to the invention onto the chip surface along the channels, the channels are rinsed with pure water and the stamp and chip separated. In a next step, the whole surface can be dipped to attach another polyionic copolymer B such as a functionalized polyionic copolymer. The product is a surface with an array of lines A/B/A/B/ etc. The lines of such an array may have width from the mm scale to the micron or submicron range. Alternatively, the fluidic patterning can be applied once more with a different stamp pattern or with the same pattern but at a different angle, e.g. at right angle to the first pattern, forming a rectangular or square array. In a subsequent step, the lines B that have reactive functional groups can be reacted with a suitable recognition molecule such as an antibody for proteins or a single stranded DNA or RNA fragment. This can be done by precision ink jet techniques, by stamping or—again—by microfluid patterning using a different or differently oriented pattern.

Another technique that allows the formation of specific patterns using polyionic copolymers is micro contact printing ($\mu$cP). A polymer stamp with a three-dimensionally structure surface is impregnated with the polyionic copolymer and transferred in a stamping process to the flat chip surface.

A third alternative is to start with a patterned sensor chip surface fabricated e.g. by a lithographic technique. The pattern has regions of positively and negatively charged surfaces. An example is a surface with square islands made from niobium oxide in a sea of aluminium oxide. If this surface is brought into contact with an aqueous solution of a polyanionic copolymer according to the invention at neutral or near neutral pH, only the positively charged aluminum oxide surface (and not the negatively charged niobium oxide pattern) will be coated by the negatively charged polymer. The opposite situation holds for a polycationic copolymer.

A fourth technique is mechanical patterning where the polymer is locally applied through spotting techniques using instruments such as pencils or capillaries.

These techniques can be used to make both types of patterns: islands formed by modified or functionalized polymer in a sea of non-modified polymer or vice versa. Also, the locally adsorbed polymers may be combined with other type of molecules to backfill empty space at the surface.

VI. Applications

The materials described here have a variety of applications in the area of substrates or devices (called 'chips' in the general sense) for analytical or sensing purposes. In particular, they are suited for the surface treatment of chips intended to be used in analytical or sensing applications where the aim is specific detection of biologically or medically relevant molecules such as peptides, proteins, oligonucleotides, DNA or RNA fragments or generally any type of antigen-antibody or key-loch type of assays. Particularly if the analyte contains a variety of molecules or ionic species, and if the aim is either to specifically detect one molecule or ion out of the many components or several molecules or ions out of the many components, the invention provides a suitable basis for producing the necessary properties of the chip surface: 1) the ability to withstand non-specific adsorption and 2) the ability to introduce in a controlled way a certain concentration of recognition entities, which will during the analytical or sensing operation interact specifically with the target molecules or ions in the analyte. If combined with suitable analytical or sensor detection methods, the invention provides the feasibility to produce chips that have both high specificity and high detection sensitivity in any type of analytical or sensing assay, in particular in bioaffinity type of assays.

The materials described here additionally have a variety of applications in the area of substrates or devices which are not "chip" based applications. In particular, for use in analytical or sensing applications where the aim is specific detection of biologically or medically relevant molecules such as peptides, proteins, oligonucleotides, DNA or RNA fragments or generally any type of antigen-antibody or key-loch type of assays. Particularly if the analyte contains a variety of molecules or ionic species, and if the aim is either to specifically detect one molecule or ion out of the many components or several molecules or ions out of the many components, the materials and methods described herein provide a suitable basis for producing the necessary properties of the chip surface: 1) the ability to withstand non-specific adsorption and 2) the ability to introduce in a controlled way a certain concentration of recognition entities, which will during the analytical or sensing operation interact specifically with the target molecules or ions in the analyte. If combined with suitable analytical or sensor detection methods, the methods provides the feasibility to produce assay surfaces that have both high specificity and high detection sensitivity in any type of analytical or sensing assay, in particular in bioaffinity type of assays.

In substrates and surfaces that interact with cells, whether in vitro or in vivo, the interaction between the cell and its substrate plays an important role in controlling its behavior. As in the other bioanalytical systems, the dual issues of prevention of nonspecific interactions and presentation of specific ligands is relevant. In this case, the nonspecific adsorbates of concern are adhesion-promoting proteins and polysaccharides, as well as other biopolymeric materials present in biological fluids. For example, the number of adhesion proteins present in blood plasma or serum is very high, and as such it is difficult to obtain a biospecific response in the absence of biospecific interactions. A multifunctional polymer may be used to suppress the nonspecific adsorption of these components in biological fluids. Moreover, a specific ligand or group of ligands can be incorporated into the multifunctional polymer, preferably at or near the termini of the chains that prevent the nonspecific interactions. Such ligands can the bind to a more limited set of cell-surface receptors than would otherwise be achieved with the spontaneously and nonspecifically adsorbing components. This can be useful in bioanalytical cell culture systems, in extracorporal therapeutic systems, and in implanted devices.

The methods can be applied to chips for any type of qualitative, semiquantitative or quantitative analytical or sensing assay. Particularly suitable detection techniques to be combined with chips include:

1) The optical waveguide technique, where the evanescent field is used to interact with and detect the amount of target molecules adsorbed to the chips surface. The technique relies on incoupling white or monochromatic light into a waveguiding layer through an optical coupling element, preferably a diffraction grating or holographic structure. The light travels within the waveguiding layer through total internal reflection. The evanescent wave, extending out of the plane of the waveguide by typically 50 to 200 nm interacts with molecules that are close (e.g. adsorbed or otherwise immobilized) to the surface. In the configuration of grating coupler sensors, typically the incoupling angles $\alpha$(TE) and/or $\alpha$ (TM) for electric and magnetic modes are measured, which are altered upon molecular adsorption or desorption onto/from the incoupling grating, due to the resulting changes of the so-called effective refractive index. The effective refractive indices N(TE), N(TM) are calculated for the observed coupling angles on the basis of incoupling condition. Supposing that N(TE), N(TM) has been calculated and the optical parameters of the waveguide layer (nF,dF), of the substrate (nS), of the covering medium (nC) are known, the refractive index (nA) and the thickness (dA) of the added layer can be calculated. Using the model that the refractive index in the adsorbed layer linearly depends on the concentration of the adsorbed material, the mass per area of the adsorbed material can be calculated.

2) Fluorescence spectroscopy or microscopy where fluorescently labeled target molecules are quantitatively analyzed by measuring the intensity of the fluorescence light.

3) Combination of 1) and 2), where the evanescent optical field is used to excite the fluorescence tags of target or tracer molecules adsorbed onto the chip surface modified. The fluorescence is detected using a fluorescence detector situated on the side opposite to the liquid flow cell. This technique is particularly suitable in view of the very high detection sensitivity of the fluorescence technique in combination with the advantage that practically only the labeled molecules attached to the surface are fluorescence-excited, with minimal contribution from 'bulk' fluorescence. The combination of the surface treatment of the chip with this analytical procedure based on evanescent field excited fluorescence detection allows detection with extreme analytical sensitivity and selectivity down to the level of only a few hundred molecules or so.

Therefore, a preferred detection technique is the specific detection of target molecules of one or more analytes in a liquid sample, wherein analyte-specific capture or recognition molecules are immobilized at the polyionic copolymer treated surface of the chip comprising an optical waveguide, fluorescently labeled analyte or analyte analogue or tracer molecules are brought into contact with this surface, excitation light is launched into the waveguiding layer (a), and the fluorescence from the fluorescent labels and generated in the evanescent field of the optical waveguide is detected. Spectrally selective optical components, such as interference filters or bandpass filters (e.g. longpass filters), or combinations thereof in the optical emission path is helpful to improve the sensitivity and improve the discrimination of background light or scattered excitation light.

4) The Surface Plasmon Resonance Technique (SPR) where the interaction of surface plasmons in thin metal films resonance condition, i.e., the resonant incidence angle for the escitation of a surface plasmon in a thin metal film, is changed upon molecular adsorption or desorption into/from the metal film, due to the resulting change of the effective refractive index.

5) Ultraviolet or Visible (UV/VIS) Spectroscopy where the adsorption at a particular characteristic wavelength is used to quantitfy the amount of target molecules adsorbed or attached to the modified surface.

6) Infrared Techniques such as Fourier Transform Infrared (FTIR) Spectroscopy, where the excitation of atomic or molecular vibrations in the infrared region is used to detect and quantify target molecules that have previously been adsorbed or attached to the surface modified chips. Surface or interface sensitive forms of IR spectroscopy such as Attenuated Total Reflection Spectroscopy (ATR-FTIR) or Infrared Reflection-Adsorption Spectroscopy (IRAS) are particularly suitable techniques.

7) Raman Spectroscopy (RS) to detect specific vibrational levels in the molecule adsorbed or attached onto the modified chip surface. Surface- or interface-sensitive types of RS are particularly suitable, e.g. Surface Enhanced Raman Spectroscopy (SERS).

8) Electrochemical techniques where for example the current or charge for the reduction or oxidation of a particular target molecule or part of that molecule is measured at a given potential. Chip based devices can also be assayed with standard fluorescence or adsorption techniques in which excitation is through light reflected off the substrate surface as opposed to the evanescent field interaction.

Other analytical or bioanalytical device surfaces can be used for qualitative, semiquantitative or quantitative analytical or sensing assays. Non "chip" based substrates also includes fiberoptic substrates. In the case of fiberoptics, techniques as described for "chip" substrates are applicable. For other non "chip" based substrates which do not support evanescent field excitation or are not a "chip", suitable techniques are described below.

1) Fluorescence spectroscopy or microscopy where fluorescently labeled target molecules are quantitatively analyzed by measuring the intensity of the fluorescence light. The fluorescence is detected using standard detectors positioned either for transmission, or more preferably, for reflection based detection methods. This technique is particularly suitable in view of the very high detection sensitivity of the fluorescence technique for fluorophores with high emission and excitation cross sections in combination with the advantage that practically only the labeled molecules attached to the surface are fluorescence-excited, with minimal contribution from 'bulk' fluorescence. Sensitivity may be additionally improved by conventional methods such as the use of filters to eliminate scatter from the excitation source into the detector or the use of higher sensitivity detectors such as cooled charge coupled devices (CCDs).

2) Adsorption spectroscopy where the adsorption at a particular characteristic wavelength is used to quantitfy the amount of target molecules adsorbed or attached to the surface modified according to the invention through reflection or transmission techniques. For simple assay formats such as lateral flow assays, the detection by visual inspection of a color change in the assay region. The adsorption can cover the wavelength range from the near Infrared to the visible region of the spectrum. The signal can be generated by either a tagged molecule or, as in the case of enzyme linked immunosorbent assays (ELISA) through an enzymatic reaction that generates a colored precipitate. In the latter case, the amount of analyte can be correlated to the precipitate adsorption.

3) Infrared Techniques such as Fourier Transform Infrared (FTIR) Spectroscopy, where the excitation of atomic or molecular vibrations in the infrared region is used to detect and quantify target molecules that have previously been adsorbed or attached to the modified chip surface. Surface or interface sensitive forms of IR spectroscopy such as Infrared Reflection-Adsorption Spectroscopy (IRAS) are particularly suitable techniques.

4) Electrochemical techniques where for example the current or charge for the reduction or oxidation of a particular target molecule or part of that molecule is measured at a given potential.

The analytical or sensor chips can be used in a variety of ways.

Non-modified and modified copolymers can be adsorbed onto suitable surfaces either in pure form or as mixtures. The optimum choice depends on the type and concentration of the target molecules and on the type of detection technique. Furthermore, the technique is particularly suited for the modification of chips to be used in assays where multiple analytes are determined on one chip, either sequentially or simultaneously.

Examples are microarrays for multipurpose DNA and RNA bioaffinity analysis 'Genomics Chips', for protein recognition and analysis based on sets of antibody-antigen recognition and analyze (Proteomics Chips). Such techniques are particularly efficient for the analysis of a multitude of components on one miniaturized chip for applications in biomedical, diagnostic DNA/RNA, or protein sensors or for the purpose of establishing extended libraries in genomics and proteomics. The suitability of these materials for the production of such chips results from the fact that polyionic copolymers can be used for easy and efficient patterning of the chip surface into areas with non-interactive properties and areas of specific interaction. Since the above mentioned multipurpose, array type of techniques often make extensive use of microfluidic techniques and networks, the surface modification and functionalization using the copolymers describes herein is particularly suitable to be combined with the microarray approach. The fluidic network can be used to specifically treat localized areas of the chip within the fluidic network, since the technique of modifying the chip surface a simple, fast, cost-effective, spontaneous adsorption process out of an aqueous solution and therefore fully compatible with the microfluidic analytical and sensing concepts.

From the viewpoint of the detection step, there are two basic alternatives:
1) In a type of batch process where the chip is functionalized. In a fluid manifold, one or several analytes and reagents are locally applied to the chip surface. After awaiting the completion or near completion of the bioaffinity reaction (incubation step), the chip is washed in a buffer and analyzed using one or a combination of the methods described above.
2) In a continuous process where the chip is functionalized and is part of a gaseous or liquid cell or flow-through cell. The conditioning of the surface can be done in a continuous and continuously monitored process within that liquid or flow-through cell, followed by in situ monitoring of the signal due to the specific interaction and adsorption or attachment of the specific target molecule in the analyte solution. The original surface of the chip may afterwards be restored/regenerated again and conditioned for the immediately following next bioaffinity assay. This may be repeated many times.

In a related but different area, the surface treatment of chips has applications in biosensors, where the aim is to attach and organize living cells in a defined manner on such chips. Since protein adsorption and cell attachment is closely related, this opens the possibility to organize cells on chips in defined way. This can be done by patterning a chip surface into areas that are non-interactive to proteins and therefore cells (e.g. areas with adsorbed non-functionalized PEG-grafted polyionic copolymer) and areas which interact with several or one cell-adhesive protein and where therefore cell attachment, will occur. The latter can be areas without adsorbed non-functionalized PEG-grafted polyionic copolymer or with adsorbed functionalized PEG-grafted polyionic copolymer whereby the function is one that induces interactions with the cell (membrane) e.g. via specific peptides that interact with integrin receptors in the cell membrane.

The detection of specific areas of the pattern can be localized to the specific areas, or can be performed for multiple specific areas simultaneously. In general, an important aspect is the sequential or simultaneous determination of multiple analytes in one or more liquid samples, where the patterned surface is used in microarray assays for the determination of analytes of the group formed of peptides, proteins, antibodies or antigens, receptors or their ligands, chelators or "histidin tag components", oligonucleotides, polynucleotides, DNA, and RNA fragments, enzymes, enzyme cofactors or inhibitors, lectins, carbohydrates. The one or more liquid samples may comprise body fluids, such as blood, serum, plasm, lymph, urine or tissue fluids or egg yolk. They also may comprise optically opaque fluids, surface water, soil or plant extracts, bio or process broths, or samples from biological tissue.

In summary, the materials and methods described herein can be used in many application areas, e.g., for the quantitative or qualitative determination of chemical, biochemical or biological analytes in screening assays in pharmacological research, combinatorial chemistry, clinical or preclinical development, for real-time binding studies or the determination of kinetic parameters in affinity screening or in research, for DNA and RNA analytics and the determination of genomic or proteomic differences in the genome, such as single nucleotide polymorphisms, for the determination of protein-DNA interactions, for the determination of regulation mechanisms for mRNA expression and protein (bio) synthesis, for toxicological studies and the determination of expression profiles, especially for the determination of biological or chemical markers, such as mRNA, proteins, peptides or lowmolecular organic (messanger) compounds, for the determination of antigens, pathogens or bacteria in pharmacological product research and development, human and veterinary diagnostics, agrochemical product research and development, symptomatic and presymptomatic plant diagnostics, for patient stratification in pharmaceutical product development and for the therapeutic drug selection, for the determination of pathogens, harmful compounds or germs, especially of salmonella, prions, viruses and bacteria, especially in nutritional and environmental analytics.

The present invention will be further understood by reference to the following non-limiting examples.

EXAMPLE 1

PLL Grafted with Monomethoxy PET, PLL-g-PEG; Application to Wave Guide Substrate The following describes the use of PLL grafted with non-modified monomethoxy PET, PLL-g-PEG, for which the polymer architecture has been optimized to achieve optimum or close to optimum protein resistance for application in analytical or sensing tasks. For clarity, the following system of abbreviations will be used when referring to the various polymers discussed in this paper: PLL(mol. wt. PLL)-g[graft ratio]-PEG(mol. wt. PEG) signifies that the graft copolymer has a PLL backbone of molecular weight of (mol. wt. PLL) in kD, a graft ratio of lysine-mer/PEG side chain and PEG side chains of molecular weight (mol. wt. PEG) in kD.

Synthesis of PLL-g-PEG

Table 1 shows the details of the masses and solvents that were used to synthesize the different polymers according to the following procedure. PLL of mol. wt. 20,000 or 375,000 (Sigma, St. Louis, Mo., USA) was dissolved in 50 mM sodium borate buffer (SBB), pH 8.5. The solution was filter sterilized (0.2 $\mu$m pore-size filter). Monomethoxy PEG-nitrophenyl carbonate, mol. wt. 5000 (Shearwater Polymers, Huntsville, Ala., USA) or hydroxysuccinimidyl ester of methoxypoly(ethylene glycol) proprionic acid mol. wt. 2000 (SPA-PEG, Shearwater Polymers Europe, Inc., NL) was either quickly dissolved with stirring in 2.5 mL 50 mM SBB, pH 8.5 or taken as a solid and added to the dissolved PLL. The reaction was allowed to proceed for 6 hr at room temperature, after which the reaction mixture was dialyzed (Spectra-Por, mol. wt. cutoff 12–14,000; Spectrum, Houston. Tex., USA) for 24 hr, first against phosphate buffered saline (PBS; 0.2 g/L KCl, 0.2 g/L $KH_2PO_4$, 8 g/L NaCl, 1.15 g/L anhydrous $Na_2HPO_4$, pH 7.4±0.1, 285 mOsm/kg $H_2O$±5%), and subsequently against deionized water. The product mixture was freeze-dried and stored at −20° C. under Ar. PLL(375)-g(5.6)-PEG(5)-$^1$H-NMR ($D_2O$): ppm-1.35, 1.60, 1.68 (—$CH_2$—); 2.88 (—$CH_2$—N—); 3.55 (PEG); 4.20 (—N—CHR—COO—). By NMR, the areas of the lysine side chain peaks were compared with the area of the PEG peak to determine the graft ratio of the comb copolymer.

A dendron copolymer (Dendron-5) was prepared according to the following procedure. Monomethoxy PEG of molecular weight 20,000 (PEG 20K; Shearwater Polymers, Huntsville, Ala., USA) was dried by azeotropic distillation from benzene. The hydroxyl terminus of the PEG was first esterified with Fmoc-Gly. The anhydride of Fmoc-Gly was produced by reaction of Fmoc-Gly (1.78 g; 8 equiv.; Novabiochem, San Diego, Calif., USA) with diisopropyl-carbodiimide (0.469 mL; 4 equiv.; DIPCDI; Aldrich) in dimethylformamide (DMF; 10 mL; anhydrous, Aldrich) and dichloromethane (DCM; 4 mL; anhydrous, Aldrich) for 30 min, room temperature with stirring under argon. The PEG (15 g; 1 equiv.) was dissolved in DCM (30 mL). Dimethylaminopyridine (91.6 mg; 1 equiv., Novabiochem) in DCM (5 mL) was added to the dissolved PEG, and this was added to the Fmoc-Gly anhydride. The vessel that contained the PEG was washed with 5 ml DCM, which was added to the reaction mixture. The reaction proceeded for 6 hr at room temperature with stirring under argon. The reaction mixture was filtered through paper under vacuum and then precipitated in cold, rapidly stirring ether, and collected by vacuum filtration. This resulting product constituted the zeroth-generation dendron copolymer. The following reaction sequence was repeated five times to yield, Dendron-5, a fifth generation dendron copolymer.

Subsequent Fmoc-protected amino acids were added to the PEG as follows. Fmoc groups on the coupled lysine residues were removed by dissolving the Fmoc-protected, lysine-grafted PEG in 20% piperidine in DMF (Perseptive Biosystems, Framingham, Mass., USA; 4 ml/g PEG 20K), heating with swirling at 45° C. until dissolved, then allowing the mixture to stand at room temperature for 30 min, followed by precipitation in cold, stirred ether, vacuum filtration and drying under vacuum, with 500 mg of each PEG-amine product retained. The Fmoc-amino acid (3 equiv.; Fmoc-L-Lys(Fmoc)-OH; Bachem, King of Prussia, Pa., USA) and HOBT (3 equiv.; Novabiochem) were dissolved in DMF (3 ml/g amino acid), and DCM (2 ml/g amino acid). DIPCDI (3 equiv.) was added, and after 15 min the PEG (2 ml DCM/g PEG) was added (the vessel that contained the PEG solution washed with 5 ml DCM, 2 times). The reaction proceeded with stirring at room temperature for at least 6 hr under argon. The reaction mixture was then precipitated in stirred cold ether, vacuum filtered, and dried under vacuum.

The dendron product was analyzed by gel-permeation chromatography (GPC) at 1% in DMF (Polymer Laboratories PL-EMD 950 evaporative mass detector; columns-Polymer Laboratories 5 μm Mixed D 300×7.5 and Polymer Laboratories 5 μm 500 Å 300×7.5 in series, Polymer Laboratories, Amherst, Mass., USA). By comparing the chromatograms from the mass detector, which allows a measurement of the mass of polymer, with the UV adsorption at 300 nm (Fmoc absorption$_{300}$=6558 L/cm mol), the percentage of coupling was calculated. Pluronics® F-108 NF and F-68 NF were obtained from BASF (Mount Olive, N.J., USA).

Sensor Chips

All of the waveguides used in this study were purchased from Microvacuum, Ltd. (Budapest, Hungary) and comprise a 1-mm-thick AF45 glass substrate, covered with a waveguiding layer with the following specifications: waveguide material (Sol-Gel technique): $Si_xTi_{1-x}O_2$, where x=0.25±0.5, refractive index ($n_F$)=1.77±0.03, thickness ($d_F$)=170–220 nm, Substrate glass slide, length (L)=12 mm, width (w)=16 mm, thickness (H)=0.55 mm, refractive index ($n_S$)=1.53, grating periodicity: 2400 lines/mm (0.4166 μm).

For experiments involving titanium and niobium oxide surfaces, an additional 14-nm-thick oxide layer was sputter coated in a Leybold dc-magnetron Z600 sputtering unit onto the waveguiding layer. All of these surfaces were characterized by XPS, AFM and ToF-SIMS. Before each experiment, the waveguides were cleaned according to the following procedure: sonication in 0.1M HCl for 10 min, extensive rinsing with ultrahigh purity water and drying under nitrogen, followed by 2 min of oxygen plasma cleaning in a Harrick Plasma Cleaner/Sterilizer PDC-32G instrument (Ossining, N.Y., USA).

Grating Coupler System

The technique involves the incoupling of excitation light beam from a He-Ne laser into a planar waveguide that allows for the direct online monitoring of macromolecule adsorption. The method is highly sensitive (i.e. ~1 ng/cm$^2$) up to a distance of 100 nm above the surface of the waveguide. The technique allows for the in situ, real time study of adsorption kinetics. Areal adsorbed mass density data were calculated from the thickness and refractive index values derived from the mode equations according to Feijter's formula. A value of 0.182 cm$^3$/g for dn/dc was used for the protein adsorption calculation, and a value of 0.202 cm$^3$/g as determined in a Raleigh interferometer was used for the PLL-g-PEG adsorption calculations. All grating coupler experiments were conducted in a BIOS-I instrument (ASI AG, Switzerland) using a Kalrez® (Dupont, USA) flow-through cell as described previously. The flow though cell was used for studying both PLL-g-PEG adsorption and protein adsorption. The flow rate and wall shear rates were 1 mL/hr and 0.83 s$^{-1}$, respectively. The calculation of adsorbed masses was done according to the following procedure:

Protocol of the Adsorption Experiments

Protocol for the Adsorption of PLL-g-PEG on Waveguide Surface.

The samples were ultrasonically cleaned in 0.1 M HCl for 10 min, extensively rinsed with ultrahigh purity water and dried in a nitrogen stream, followed by 2 min of oxygen-plasma cleaning as described earlier. PLL-g-PEG modified surfaces were prepared by dip coating for 10 min in a 1 mg/mL solution of PLL-g-PEG in 10 mM HEPES (4-(2-hydroxyethyl)piperazine-1-ethanesulfonic acid, adjusted to pH 7.4 with 1M NaOH solution). This buffer solution will be referred to as HEPES Z1 hereafter. Subsequently, the modified waveguides were rinsed immediately with ultrapure water and dried under nitrogen. Some samples were analyzed and used without a proper cleaning step as described in the sample preparation procedure to test the effect of surface contamination on the adsorption and performance of PLL-g-PEG.

Protocol for Optical Grating Coupler Experiment and Sample Preparation

Samples with adsorbed PLL-g-PEG layers were prepared as described above and dried in flowing nitrogen. Their protein and serum adsorption performance was subsequently measured in the grating coupler system as described below.

Samples modified with PLL-g-PEG in situ were initially placed in HEPES Z1 immediately following the cleaning procedure and allowed to soak overnight. Prior to assembling the flow-through cuvette in the grating coupler instrument, the samples were rinsed with ultrapure water and dried under nitrogen. These presoaked samples equilibrated and reached a flat baseline in HEPES Z1 in less than 1 hr. Then, the samples were exposed in situ to the PLL-g-PEG solution (1 mg/mL in HEPES Z1). The adsorption was subsequently monitored for 30 min. The polymer solution was then replaced with HEPES Z1, and the protein and serum adsorption performance was measured as described later.

Protocol for Grating Coupler Experiment and Sample Preparation

Samples with adsorbed PLL-g-PEG layers were prepared as described above and dried in flowing nitrogen. Their protein and serum adsorption performance was subsequently measured in the grating coupler system as described later. Samples modified with PLL-g-PEG in situ were initially placed in HEPES Z1 immediately following the cleaning procedure and allowed to soak overnight. Prior to assembling the flow-through cuvette in the grating coupler instrument, the samples were rinsed with ultrapure water and dried under nitrogen. These presoaked samples equilibrated and reached a flat baseline in HEPES Z1 in less than 1 hr. Then, the samples were exposed in situ to the PLL-g-PEG solution (1 mg/mL in HEPES Z1). The adsorption was subsequently monitored for 30 min. The polymer solution was then replaced with HEPES Z1, and the protein and serum adsorption performance was measured as described later.

$Si_{0.6}Ti_{0.4}O_2$ waveguides were used for the pH-dependence measurements and were prepared as described in the immediately preceding procedure. However, in this case, the solution was 10 mM HEPES titrated to the predetermined pH by the addition of either 1M NaOH or 1 M HCl. The polymer concentration was 0.1 mg/ml in the same pH-adjusted HEPES solution. After 1 hr of polymer adsorption and 30 min of washing with the pH adjusted solution, the solution was changed to the pH 7.4 buffer (HEPES Z1), and the protein adsorption performance was measured as described later in this section. The same procedure was used for the ionic-strength-dependence experiments, except that NaCl was used to generate the solution of predetermined ionic strength.

Protocol of the Protein Adsorption Experiments

The waveguides were exposed to a solution of human serum (Control Serum N, Art.#07 3711 9, US#42384 and human γ-globulin, Roche (Switzerland)) for 1 hr at a temperature of 25° C. and subsequently washed for 30 min in HEPES Z1. Human serum albumin (HSA), human fibrinogen and human fibronectin were obtained from Sigma Chemical Co. (USA); and their related antibodies were obtained from Dako A/S (Denmark). In the case of the single protein adsorption experiments, the waveguide was exposed to a 1 mg/mL solution of the appropriate protein in HEPES Z1 for 1 hr at a temperature of 25° C. and subsequently washed for 30 min in HEPES Z1.

In some cases after the serum exposure, the waveguide was tested against solutions of 0.1 mg/mL rabbit anti-HSA and 0.28 mg/mL rabbit anti-human fibronectin for 30 min at a temperature of 25° C. and subsequently washed for 30 min in HEPES Z1. Adsorption of human fibrinogen was tested separately by exposure to a 1 mg/mL solution of fibrinogen for 1 hr at 25° C. followed by a 0.1 mg/mL solution of rabbit anti-human fibrinogen for 30 min.

PLL(375)-g[5.6]-PEG(5) Adsorption and Protein Resistance Study

Figure 3:
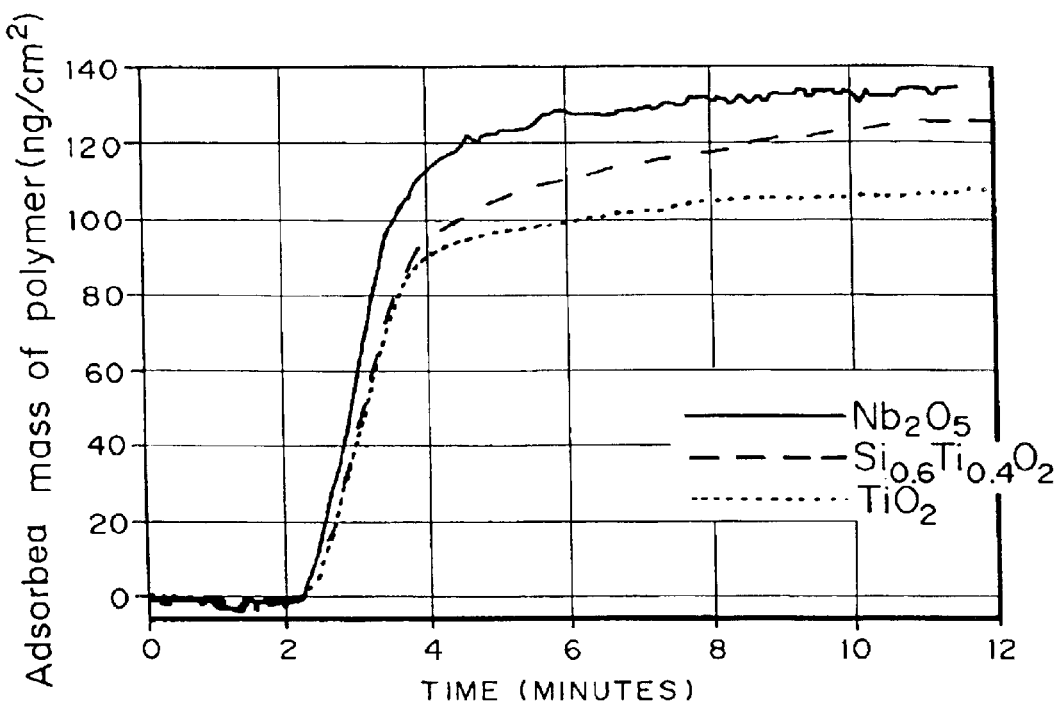
FIG. 3 is a graph showing adsorption curves of PLL(375)-g[5.6]-PEG(5) on three metal oxide surfaces as measured by the grating coupler technique. [10 mM HEPES Z1 (pH 7.4), 1 mg/mL polymer, 1 mL/hr, T=26° C.].
Figure 4:
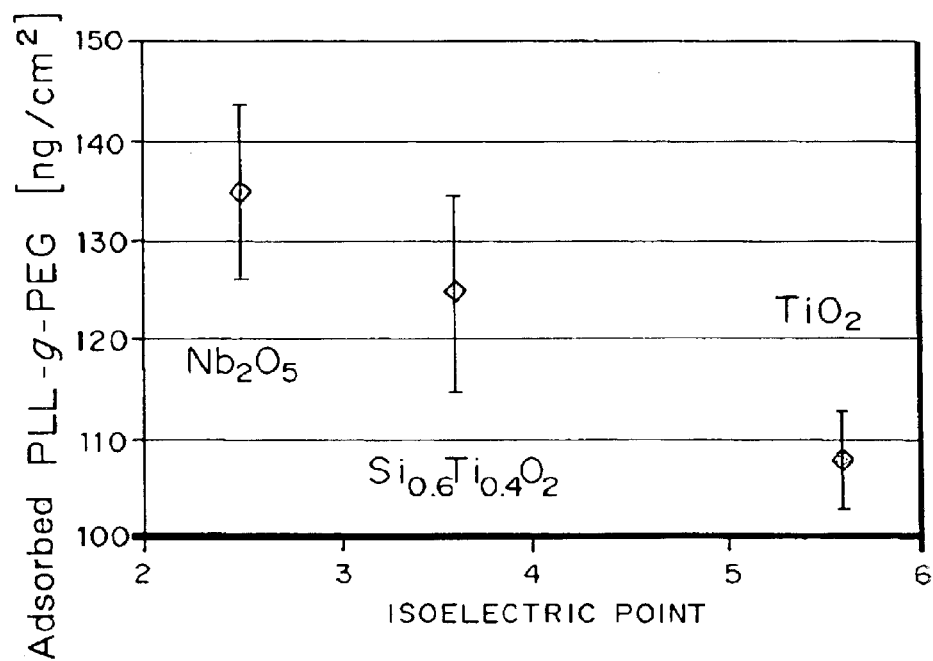
FIG. 4 is a graph showing the dependence of the adsorbed amount of PLL(375)-g[5.6]-PEG(5) on the isoelectric point of the metal oxide surfaces as measured by the optical grating coupler technique[10 mM HEPES Z1 (pH 7.4), 1 mg/mL polymer, 1 mL/hr, T=26° C.]

All of the following measurements were carried out in a flow-through cell, and both the PLL-g-PEG pretreatment and the protein-adsorption tests were carried out in situ and consecutively without an intermittent drying stage unless otherwise noted. The results from grating coupler experiments (see FIG. 3) indicate that the PLL-g-PEG polymer spontaneously adsorbed out of a pH 7.4 buffered aqueous solution onto metal oxide surfaces. The example shown in FIG. 3 involved the adsorption of the PLL-g-PEG onto three different metal oxide surfaces: titanium, niobium and silicon/titanium. This adsorption process occurred rapidly and resulted in the formation of a layer of adsorbed polymer on the surface. Typically for $Si_{0.6}TiO_{4}O_2$ surfaces, a layer with an adsorbed areal density of approximately 125 ng/cm² formed, and 95% of the final observed mass was reached within the first 5 min. Similar behavior was observed for the other two metal oxide surfaces investigated (i.e. niobium pentoxide, titanium dioxide). Although the adsorption kinetics were quite similar, the resulting amount of PLL-g-PEG adsorbed to the surface was different and depended on the characteristic isoelectric point of the metal oxide, as shown in FIG. 4 and Table 2.

Figure 5:
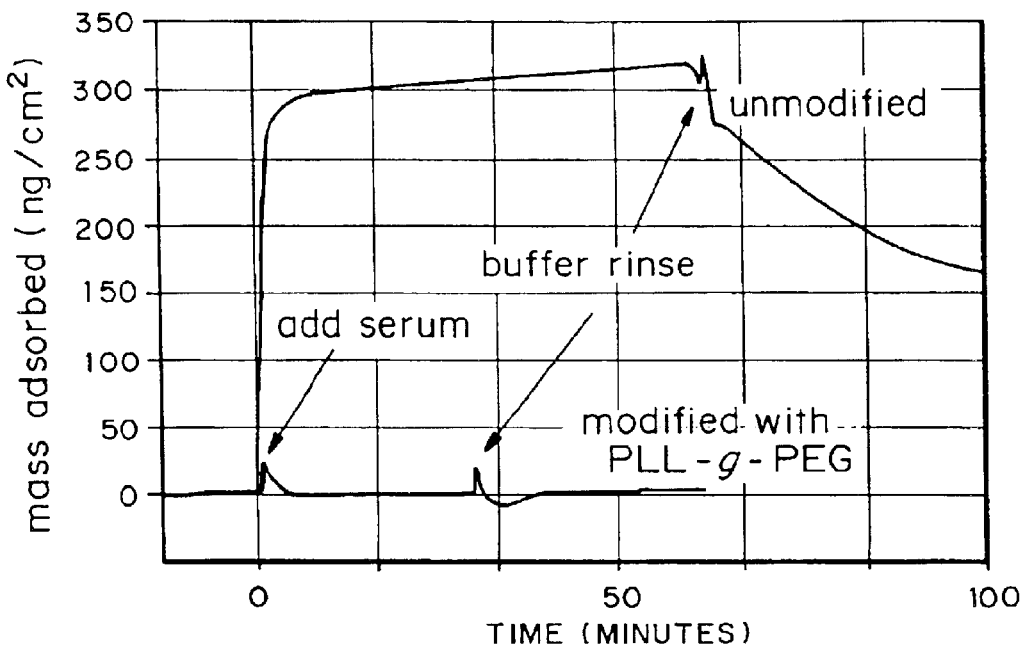
FIG. 5 is a graph of serum adsorption to either an unmodified or a PLL(375)-g[5.6]-PEG(5)-modified $Si0.6Ti0.4O_2$ surface as measured by the optical grating coupler technique. [10 mM HEPES Z1 (pH 7.4), 1 mg/mL polymer, T=26° C.] (The baseline was achieved under 10 mM HEPES Z1, and the spikes are due to temporary flow rate related pressure changes.)
Figure 6:
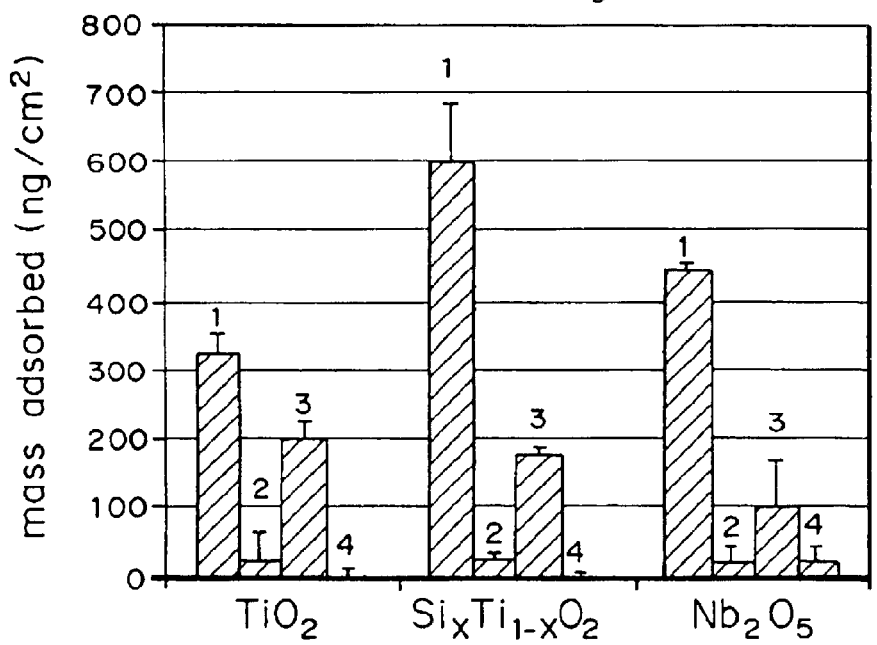
FIG. 6 is a graph of the adsorbed areal mass of serum and HSA onto PLL(375)-g[5.6]-PEG(5)-modified and unmodified $Si0.6Ti0.4O_2,TiO_2$ and $Nb_2O_5$ surfaces as measured by the optical grating coupler technique. [10 mM HEPES Z1 (pH 7.4), 1 mg/mL polymer, 1 mL/hr, T=26° C.]

Subsequent protein adsorption experiments revealed that PLL-g-PEG modification of the metal oxide surfaces resulted in sharply reduced protein adsorption. Typically, the exposure of a metal oxide surface to serum produces a layer of adsorbed protein with an areal density between 150 and 250 ng/cm² after the washing step. However, waveguides pre-coated with a self-assembled layer of PLL-g-PEG show a drastic reduction in subsequent serum protein adsorption. An example of this is shown in FIG. 5. This experiment involved modified and unmodified titanium dioxide waveguides that were prepared according to the procedure described above. Generally, PLL(375)-g[5.6]-PEG(5) pretreatment, regardless of the preparation procedure, caused an order of magnitude decrease in the areal density of adsorbed protein after serum exposure on titanium dioxide, silicon/titanium dioxide and niobium oxide surfaces (see FIG. 6). Similarly, the adsorption of human serum albumin (1 mg/mL, 10 mM HEPES buffered solution, pH 7.4) was decreased by two orders of magnitude following the PLL-g-PEG pretreatment (see FIG. 6). The quantitative protein adsorption data for all surfaces studied are listed in Table 3.

The residual material remaining on the surface after serum exposure was tested against antibodies of several common serum proteins, such as anti-albumin, anti-fibronectin, and anti-γ-globulin. These antibodies exhibited adsorbed areal density lower than that detectable by the grating coupler technique (i.e.<2 ng/cm²), which suggests that none of the proteins are present in their active conformations on the modified surfaces. It is likely that serum components other than proteins are picked up by the modified surfaces. Since serum is fibrinogen-depleted, fibrinogen was also tested separately from a 5 mg/mL solution in HEPES Z1, followed by an anti-fibrinogen assay. For PLL (375)-g[5.6]-PEG(5)-modified silicon/titanium dioxide surface, 85 ng/cm² and 150 ng/cm² of adsorbed areal density were observed for fibrinogen and anti-fibrinogen, respectively. The antibody results are not shown.

Figure 7:
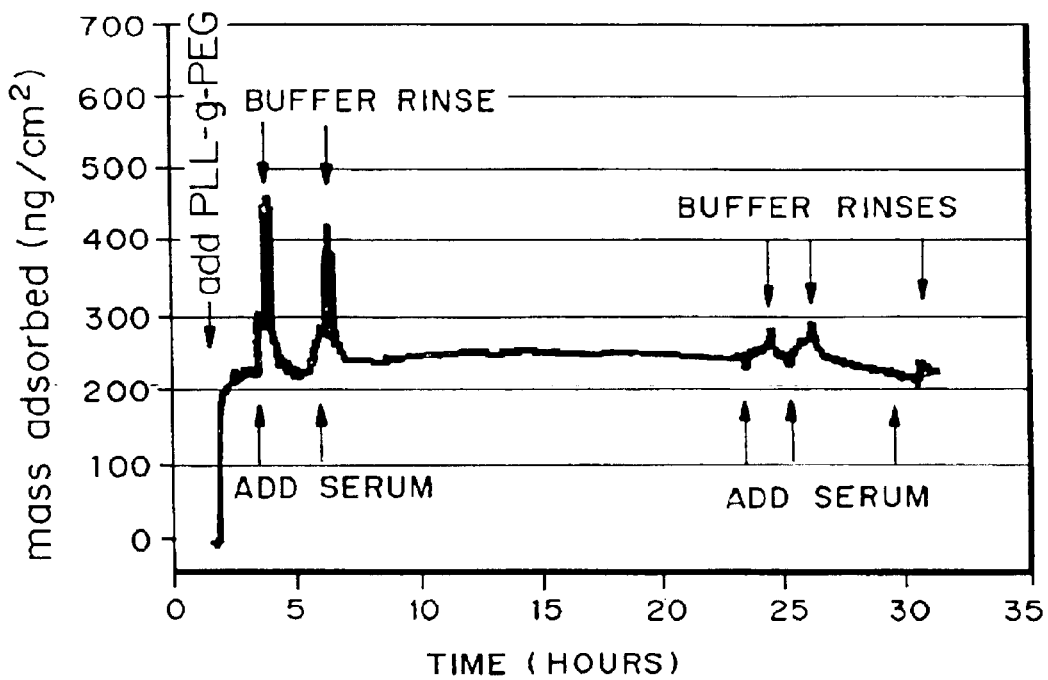
FIG. 7 is a graph of the long-term stability of the protein-adsorption suppression of a PLL(375)-g[5.6]-PEG(5)-modified $Si0.6Ti0.4O_2$ surface as measured by the optical grating coupler technique. [Polymer adsorption carried out under 10 mM HEPES Z1, 1 mg/mL polymer, 1 mL/hr, T=26° C.; serum adsorption, 1 mL/hr, T=26° C.]

Performance and Long-term Stability of the Adsorbed PLL (375)-g[5.6]-PEG(5) Layer Once established on the surface, the adsorbed layer of PLL(375)-g[5.6]-PEG(5) was found to be stable (i.e. <5% loss in mass of the adsorbed layer after one week) and resistant to protein adsorption over 24 hr at 37° C. under a flowing HEPES Z1 solution, as shown in FIG. 7. This experiment involved the in situ deposition within the first hour of a PLL(375)-g[5.6]-PEG(5) layer on the surface of a silicon/titanium dioxide waveguide. Two subsequent exposures to serum produced less than 20 ng/cm² of surface adsorbed protein. Eighteen hours later, two additional serum exposures similarly produced less than 20 ng/cm². Similar performance was observed when PBS was used as the buffer instead of HEPES Z1.

PLL(375)-g[5.6]-PEG(5) modified waveguides that were stored dry were found to retain their protein resistant properties after more than three months, and those stored in HEPES-buffered solution were found to retain their protein-resistant properties after more than one month.

Pluronics®, diblock copolymers consisting of a poly propylene oxide flanked by two polyethylene oxide chains, are commonly used to immobilize PEG onto hydrophobic surfaces. However, Pluronics® F-108 and F-68 were found not to adsorb onto any of the metal oxide surfaces investigated here and as a result did not show any protein adsorption suppressing properties.

PLL(375)-g[5.6]-PEG(5) was also found to adsorb onto a pre-adsorbed layer of serum proteins. After a typical adsorption of serum protein (i.e. about 260 ng/cm$^2$), subsequent exposure to a 1 mg/mL solution of PLL(375)-g[5.6]-PEG(5) effected an additional layer of polymer with a surface areal density of approximately 90 ng/cm$^2$.

Effect of Precontamination on PLL(375)-g[5.6]-PEG(5) Adsorption

Metal oxide surfaces that exhibited large amounts of hydrocarbon surface contamination nevertheless adsorbed a layer of PLL(375)-g[5.6]-PEG(5) that suppressed subsequent serum adsorption. Titanium dioxide waveguides that were not cleaned according to the procedure described above exhibited substantial hydrocarbon surface contamination. However, these XPS data also indicate that an additional layer of PLL(375)-g[5.6]-PEG(5) does indeed adsorb onto this contaminated surface. Furthermore, optical grating coupler experiments showed that the typical adsorbed areal density of 120 ng/cm$^2$ forms on contaminated titanium dioxide waveguides and that this adsorbed layer of polymer suppresses subsequent serum protein adsorption by about 95%. That is, the adsorption and performance characteristics of the PLL(375)-g[5.6]-PEG(5) are identical in the case of both contaminated and cleaned titanium dioxide surfaces.

Effect of Polymer Architecture on Protein Interactions

Alternative architectures of the polymer were explored for the suppression of protein adsorption performance. These architectures included brush-like graft copolymers with differing PEG side-chain length, PLL backbone length and PEG grafting ratio (see Table 1). The inverted tree-like dendrimeric PLL having a single PEG side chain attached at the base was also investigated.

Effect of the Backbone (PLL) Structure on Subsequent Protein Adsorption

Figure 8:
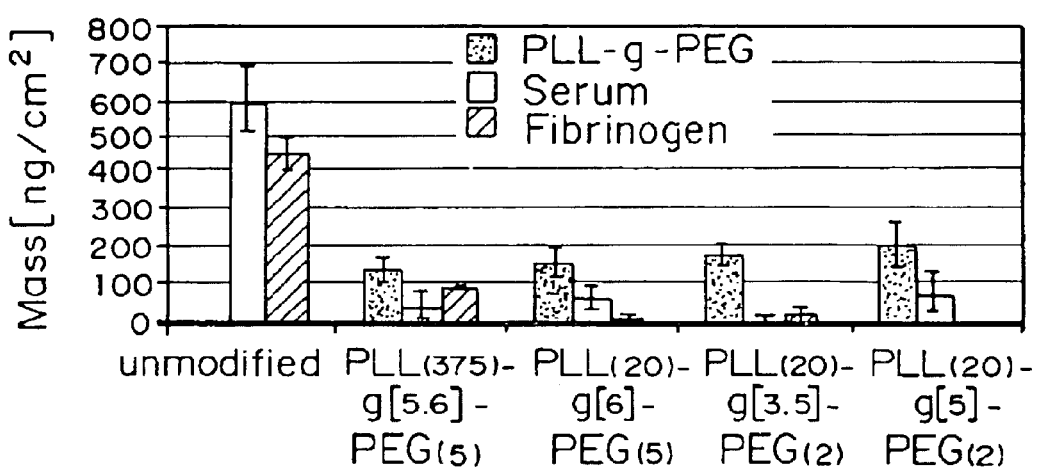
FIG. 8 is a graph of the effect of polymer architecture on the adsorbed areal density of the copolymer and subsequent serum on $Si0.6Ti0.4O_2$ surfaces as measured by the optical grating coupler technique. [Polymer adsorption carried out under 10 mM HEPES Z1, 1 mg/mL polymer, 1 mL/hr, T=26° C.; serum adsorption, 1 mL/hr, T=26° C.]

The graft copolymer architecture was found to influence the subsequent serum adsorption suppression. All of the polymers investigated demonstrate adsorption on silicon/titanium dioxide surfaces in the areal density range of about 150 ng/cm$^2$, as shown in FIG. 8. Of the two comb copolymers with PEG side chain mol. wt. of 5000, the PLL(375)-g[5.6]-PEG(5) demonstrates only a slightly more pronounced suppression of serum adsorption, decreasing the observed adsorption by about 90% to 30 ng/cm$^2$. The graft copolymer with the lower mol. wt., (PLL(20)-g[6.0]-PEG(5)), decreases the observed protein adsorption from serum exposure by about 85% to 50 ng/cm$^2$. Dendron-5, consisting of a 20,000 mol. wt. PEG with a terminus consisting of a five generation lysine dendrimer, was also found to adsorb onto silicon/titanium dioxide surfaces in the areal density range of 120 to 150 ng/cm$^2$. Furthermore, this adsorbed polymer layer was found to decrease the subsequent protein adsorption due to serum exposure by about 75% to 80 ng/cm$^2$.

Effect of the Copolymer Grafting Ratio on Subsequent Protein Adsorption

The grafting ratio was also found to influence the subsequent serum adsorption performance. To explore the effect of the grafting ratio on the polymer adsorption and subsequent protein resistance behavior, PLL(20)-g[3.5]-PEG(2) and PLL(20)-g[5]-PEG(2) were synthesized. These two polymers differ only in their respective grafting ratios of 3.5:1 and 5.0:1 (i.e. lysine monomer: PEG side chain). As shown in FIG. 8, PLL(20)-g[3.5]-PEG(2) and PLL(20)-g[5]-PEG(2) exhibited adsorbed mass densities of 170 and 190 ng/cm$^2$, respectively. However, PLL(20)-g[3.5]-PEG(2) demonstrated far greater suppression of protein adsorption (i.e. a 99% decrease vs. an 80% decrease for the PLL(20)-g[5]-PEG(2)). In fact, the PLL(20)-g[3.5]-PEG(2) demonstrated the greatest suppression of protein adsorption from serum of all of the polymers investigated in this study. This amount of adsorbed mass is approximately of the same magnitude as the detection limit of the grating coupler technique (i.e. ~1 ng/cm$^2$) (see Table 3).

TABLE 1

Details of synthesis of the different types of PLL-g-PEG. (SBB is sodium borate buffer (pH = 8.5), and STBB is sodium tetraborate buffer (pH = 8.5).) All of the molecular weights are in kD.

| Polymer PLL(mol. wt. PLL)-g[Lysine/PEG side chain]-PEG(mol. wt. PEG) | PLL | PEG |
|---|---|---|
| PLL(375)-g[5.6]-PEG(5) | 500 mg in 10 mL SBB | 2.0 g in 2.5 mL SBB |
| PLL(20)-g[6.0]-PEG(5) | 500 mg in 10 mL SBB | 2.0 g in 2.5 mL SBB |
| PLL(20)-g[3.5]-PEG(2) | 83.6 mg in 1.05 mL STBB | 215.7 mg solid |
| PLL(20)-g[5.5]-PEG(2) | 106.8 mg in 1.34 mL STBB | 193.2 mg solid |

TABLE 2

Summary of the isoelectric points and the charge densities of the investigated surfaces and the observed adsorbed areal density of PLL(375)-g[5.6]-PEG(5), serum and human serum albumin (HSA) on unmodified surfaces and of serum and HSA on PLL(375)-g[5.6]-PEG(5)-modified surfaces. [Polymer adsorption carried out under 10 mM HEPES Z1,1 mg/mL polymer, 1 mL/hr, T = 26° C.; serum adsorption, 1 mL/hr, T = 26° C.; HSA adsorption, 10 mM HEPES Z1, 1 mg/mL, 1 mL/hr, T = 26° C.]. (Reference for isoelectric points: P. Tengvall, I. Lundstrom, Clinical Materials 9 (1992) 115–134)

| Substrate | Isoelectric point*) | Surface charge [uC/cm$^2$] | Adsorbed mass of PLL(375)-g(5.6)-PLL(5) [ng/cm$^2$] | Adsorbed mass of serum onto an untreated surface [ng/cm$^2$] | Adsorbed mass of serum onto a PLL(375)-g(5.6)-PLL(5) treated surface [ng/cm$^2$] | Adsorbed mass of HSA onto an untreated surface [ng/cm$^2$] | Adsorbed mass of HSA onto a PLL(375)-g(5.6)-PLL(5) treated surface [ng/cm$^2$] |
|---|---|---|---|---|---|---|---|
| TiO$_2$ | 5.6 | 5 | 108 | 320 | 20 | 200 | <1.0 |
| Si$_{0.4}$Ti$_{0.6}$O$_2$ | 3.6 | 25 | 125 | 270 | 25 | 176 | <1.0 |
| Nb$_2$O$_5$ | 2.5 | 50 | 135 | 445 | 19 | 96 | 24 |

TABLE 3

The observed adsorbed areal density of polymer, serum, and fibrinogen on surfaces modified with various PLL-g-PEG copolymers. [Polymer adsorption carried out under 10 mM HEPES Z1, 1 mg/mL polymer, 1 mL/hr, T = 26° C.; serum adsorption, 1 mL/hr, T = 26° C.; fibrinogen adsorption, 10 mM HEPES Z1, 1 mg/mL, 1 mL/hr, T = 26° C.]

| Surface | Adsorbed mass of PLL-g-PLL polymer [ng/cm$^2$] | Adsorbed mass of serum [ng/cm$^2$] | Adsorbed mass of fibrinogen [ng/cm$^2$] |
|---|---|---|---|
| Unmodified Si$_{0.4}$Ti$_{0.6}$O$_2$ | — | 270 | 451 |
| PLL(375)-g[5.6]-PEG(5) | 133 | 30 | 85 |
| PLL(20)-g[6]-PEG(5) | 152 | 50 | 3 |
| PLL(20)-g[3.5]-PEG(2) | 169 | 3 | 15 |
| PLL(20)-g[5]-PEG(2) | 194 | 63 | 1 |

EXAMPLE 2

Application of Biotin-modified PEG-grafted PLL

This example refers to the use of biotin-modified PEG-grafted PLL for application on chips for bioaffinity sensor assays using the biotin-streptavidin-biotin recognition assay.

Synthesis of the Functionalized, Biotinylated Copolymer

PLL of mol. wt. 20,000 (Sigma, CH) was dissolved in 50 mM sodium tetraborate buffer, pH 8.5 at a concentration of 40 mg/ml. The solution was filter sterilized (0.2 gm pore-size filter). Solid n-hydroxysuccinimidyl ester of methoxypoly(ethylene glycol) proprionic acid (mol. wt. 2,000) (SPA-10 PEG, Shearwater Polymers Europe, Inc., NL), and -biotin, -hydroxysuccinimidyl ester of poly (ethylene glycol)-carbonate (mol. wt. 3,400) (NHS-PEG-biotin, Shearwater Polymers Europe, Inc., NL) in the desired stochiometric ratio were added to the dissolved PLL solution. The reaction was allowed to proceed for 6 hr at room temperature, after which the reaction mixture was dialyzed (Spectra/Por, MWCO 6–8000, Spectrum, Socochim, CH) against phosphate buffer saline (PBS) for 24 hrs and subsequently against deionised water for 24 hrs. The dialyzed solution was lyophilized for 48 hrs and stored under nitrogen at −25° C.

Four PLL-g-PEG polymers PLL(20)-g[3.5]-{(PEG(2)}$_x$, {PEG(3.4)-biotin}$_{1-x}$, with a Lys:PEG ratio of 3.5:1, yielding the greatest suppression of protein adsorption from serum as shown from Example 1, and different amounts of biotin 0% (x=1),10%a and 10%b (2 polymers) (x=0.9) and 50% (x=0.5) of the PEG chains are biotinylated) were synthesized. In the case of PLL-g-PEG-Biotin 10%b, the NHS-PEG-biotin was added first and reaction allowed for 1 hr before adding the SPA-PEG. Table 4 reports the quantity of material used.

Size Exclusion Chromatography

Size exclusion chromatography analysis of the polymers was performed in 0.2 M sodium carbonate/bicarbonate buffer solution pH 10 with a Shodex Ohpak column, SB-894HQ (Alltech, Deerfield, Ill.-USA). Molecular weights of the different polymers with Lys:PEG of 3.5:1 were all in the range of 70 kD. Molecular weights of PLL-g-PEG with Lys:PEG of 2:1 and 5:1 were approximately 100 kD and 55 kD, respectively.

Comparative and Absolute Measurement of the Enzymatic Activity of Streptavidin-horseradish Peroxidase Conjugate Immobilized on the Biotinylated PLL-g-PEG Polymers Substrates For this assay, substrates consisted of 20 nm of pure titanium dioxide (TiO$_2$) produced by physical vapor deposition onto a silicon wafer. The RMS roughness of the TiO$_2$ coating determined via AFM (Bioscope, Digital Instruments) was 0.3 nm (scanned surface: 5×5 $\mu$m$^2$). The wafer was sampled into pieces of 1 cm$^2$ and these were ultrasonically cleaned in acetone (uvasol, Merck) and 2-propanol (uvasol, Merck) for 5 min. each, dried under nitrogen (5.0) and subsequently cleaned by oxygen plasma (plasma cleaner/sterilizer PDC-32G, Harrick) for 3 min.

PLL-g-PEG Self-assembly

Solutions of PLL-g-PEG-OCH$_3$,PLL-g-PEG-Biotin (10%a), PLL-g-PEG-Biotin(10%b) and PLL-g-PEG-Biotin (50%) were prepared in 10 mM HEPES buffer pH 7.4, at a concentration of 1 mg/ml and filter-sterilized (0.22 $\mu$m Durapore Millex, Sigma-CH). Self-assembly of the different polymers on TiO$_2$ (3 samples per polymer type) proceeded for 90 min. Samples were then rinsed extensively with filter-sterilized HEPES buffer pH 7.4 and dried under nitrogen (5.0). Three bare TiO$_2$ samples were also preserved as references.

Streptavidin Horseradish Peroxidase Adsorption

The samples were distributed in a 6-wells plate and covered with 4 ml of a solution of streptavidin-horseradish peroxidase conjugate in PBS pH 7.4, diluted to 1/1000 in HEPES buffer (pH 7.4). (horseradish peroxidase (HRP) to streptavidin molecular ratio is 5:1; 400 ng streptavidin/1200 ng horseradish peroxidase). Samples were left for incubation at room temperature for 60 min. They were then rinsed extensively with fresh HEPES buffer and subsequently with sodium acetate/citric acid buffer pH 6.0.

Quantification of the Enzymatic Activity of the Chemisorbed Streptavidin Horseradish Peroxidase The samples were immediately transferred into individual wells of a 24-wells plate and incubated at room temperature under gentle shaking in 1.6 ml of a 0.42 mM solution of 3,3'14 5,5'-tetramethylbenzidine (TMB, Merck-CH) in sodium acetate/citric acid buffer (pH 6.0, containing 0.004% (v/v) H$_2$O$_2$ and 1% DMSO, previously used to dissolve the TMB). A dilution series (5 k, 10 k, 100 k, 500 k, 1M, 5M, 10M, 50M) of the streptavidin-HRP PBS solution in sodium acetate/citric acid was also prepared and incubated simultaneously under the same conditions to serve as calibration curve. After 26 min, as the solutions had visibly turned blue under the enzymatic activity of the peroxidase, the solid samples were removed from the solution and the reaction stopped by adding 100 $\mu$l of 2 M H$_2$SO$_4$. The solution was subsequently transferred into disposable cuvettes, and the absorption measured at 450 nm (JASCO 7800 UV/Vis Spectrophotometer).

Non-specific Protein Adsorption of PLL-g-PEG 2:1, 3.5:1, 5:1; Mass of Polymer Adsorbed and Choice of Optimum Polymer As can be seen from FIG. 8, when the PEG interchain spacing D is smaller or equivalent to the PEG radius of gyration, non-specific protein adsorption is efficiently prevented. On the contrary, an interchain spacing larger than the PEG radius of gyration leads to protein adsorption levels comparable to the bare TiO$_2$ surface. In addition, one can also note the difference in the polymer mass adsorbed, which is higher for the 3.5:1 PLL-g-PEG compared to the 2:1 PLL-g-PEG. This is probably related to the fewer anchoring —NH$_3^+$ groups available in the 2:1 polymer since a larger number of these side chains have been derivatized with PEG. Although the mass of polymer adsorbed at the surface of the waveguide is lower, the density of PEG chains is probably high enough to lead to chain overlapping and hence sufficient to yield a protein repellent PLL-g-PEG-methoxy interface. Nevertheless, one can argue that the lower polymer mass adsorbed as well as the fewer anchoring points in this polymer could be detrimental to the stability of the interface. Therefore, the PLL-g-PEG-methoxy polymer with a Lys:PEG ratio of 3.5:1 seems to be an optimum in our PLL-g-PEG polymer series.

Figure 9:
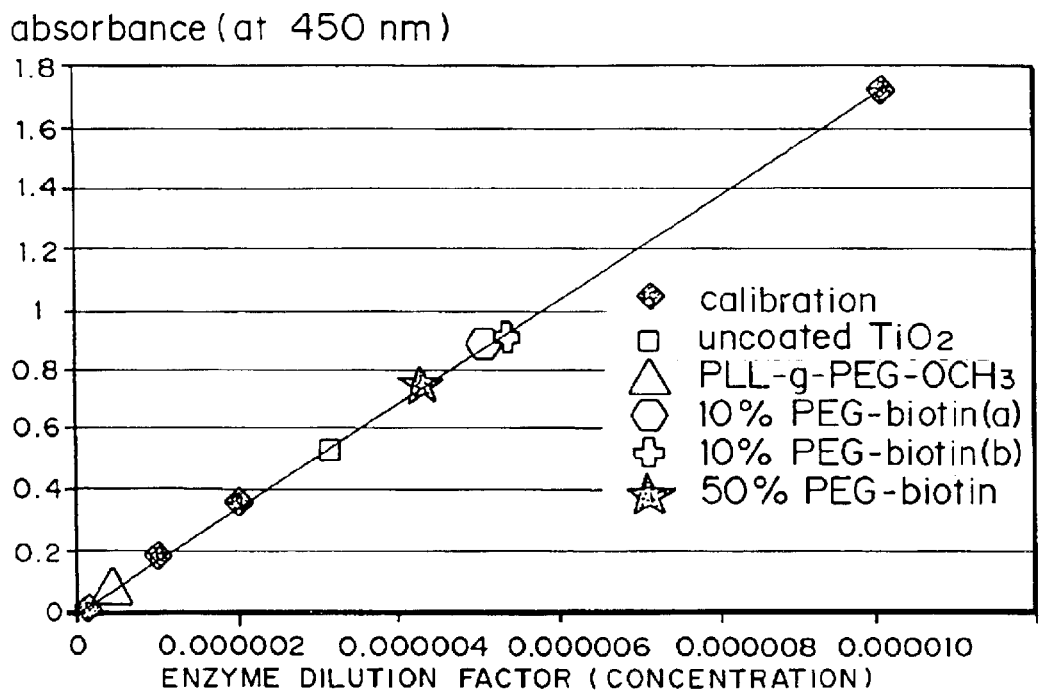
FIG. 9 is a graph of the activity of horseradish peroxidase: Titanium oxide coated with different PLL-g-PEG derivatives. The streptavidin-conjugated enzyme is immobilized via biotin, which acts as the functional group of the PLL-PEG-biotin copolymer. The non-specific binding of the enzyme onto the uncoated metal oxide as well as onto the non-functionalized PLL-g-PEG is investigated in parallel.

As can be seen from FIG. 9, activity of the peroxidase on the different surfaces ranks as follows: PLL-g-PEG-methoxy<<$TiO_2$<PLL-g-PEG-Biotin 50%<PLL-g-PEG-Biotin 10%a<PLL-g-PEG-Biotin 10%b. In parallel, from the grating coupler results, the mass of streptavidin adsorbed ranks as follows: PLL-g-PEG-methoxy (mass below the detection limit)<PLL-g-PEG-Biotin 10%a (mass<33 ng/cm$^2$)<PLL-g-PEG-Biotin 10%b (mass<99 ng/cm$^2$)<$TiO_2$ (mass<160 ng/cm$^2$)<PLL-g-PEG-Biotin 50% (mass<283 ng/cm$^2$). The extremely low peroxidase activity level on the PLL-g-PEG-methoxy (close to background noise, see FIG. 4) shows that almost no streptavidin adsorbed on the surface.

As the biotin content increases, the activity levels of the peroxidase is significantly increased, as can be seen for PLL-g-PEG-biotin 10%a and –10%b. Further increase in the biotin content (–50%) leads to a marked decrease in the peroxidase activity, although the mass of streptavidin adsorbed is higher. At this stage, the high content of biotin at the surface probably drives the unfolding of streptavidin, thus leading to lower activity. Alternatively steric hindrance of the enzyme molecules as a consequence of too high biotin density may be the cause for this observation. Finally, the bare surface shows less streptavidin adsorption in comparison to the 50% biotin case, and also lower peroxidase activity, implying that the non-specifically adsorbed streptavidin is also unfolding at the surface of the $TiO_2$ chip thus lowering the activity of the enzyme.

Specific Detection of Streptavidin on PLL-g-PEG-biotin Modified Chips Using the Grating Coupler Technique 10 mM HEPES (pH 7.4) buffer solution and $SiO_2$—$TiO_2$ waveguides (Microvacuum Ltd, H) were used for all of the experiments (details: see section 6.1.2). The modified waveguides were prepared in situ by exposing the waveguides to 50 μg/ml PLL-g-PEG-biotin polymer solution for twenty minutes in a flow cell apparatus, followed by rinsing with buffer. Then the PLL-g-PEG-biotin modified waveguides were exposed to Control Serum N (human) (Roche, CH) for thirty minutes and then washed in buffer. At the end of the measurement selectivity was tested with 1 mg/ml streptavidin (SIGMA, USA) for 20 minutes followed by a rinse with buffer. Mass data were calculated from the thickness and refractive index values derived from the mode equations (see section 5.2). All experiments were conducted in a BIOS-I instrument (ASI AG, Zürich, CH).

Figure 10:
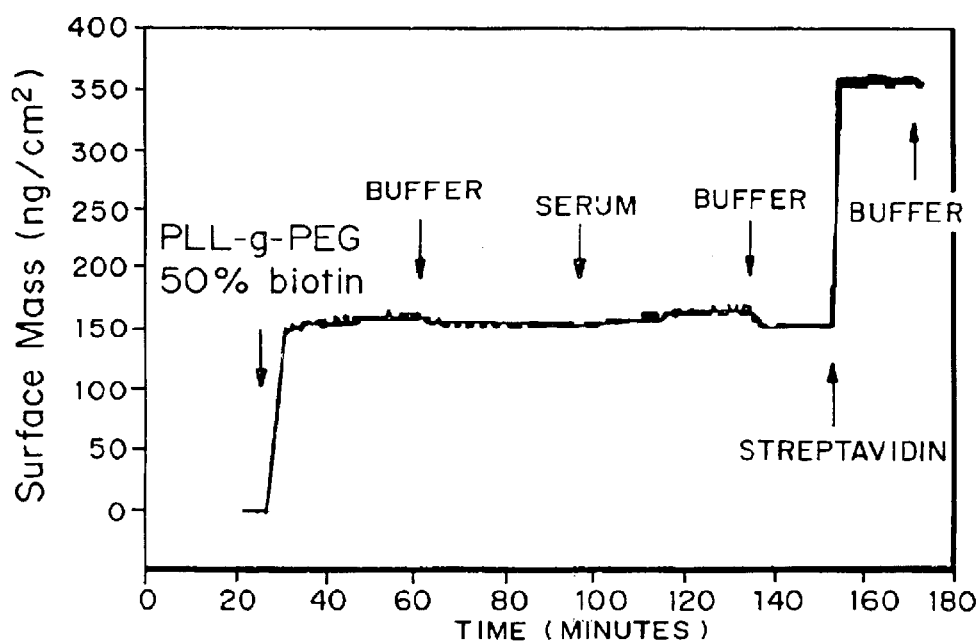
FIG. 10 is the time-resolved selective sensor response of the biotin-derivatized PLL-g-PEG-biotin (adsorbed onto a waveguide chip) to streptavidin exposure.
Figure 11:
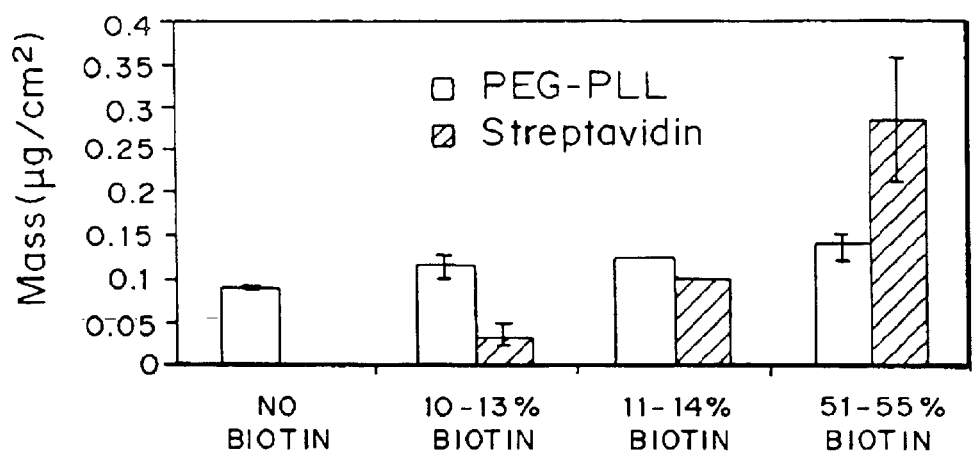
FIG. 11 is a graph of the amount of PLL-g-PEG-biotin adsorbed onto a $SixTi1-x O_2$ waveguide chip surface and the amount of streptavidin subsequently adsorbed onto the PLL-g-PEG-biotin covered chip surface for three different biotin concentrations in the PLL-g-PEG-biotin molecule (see Table 5).
Figure 12:
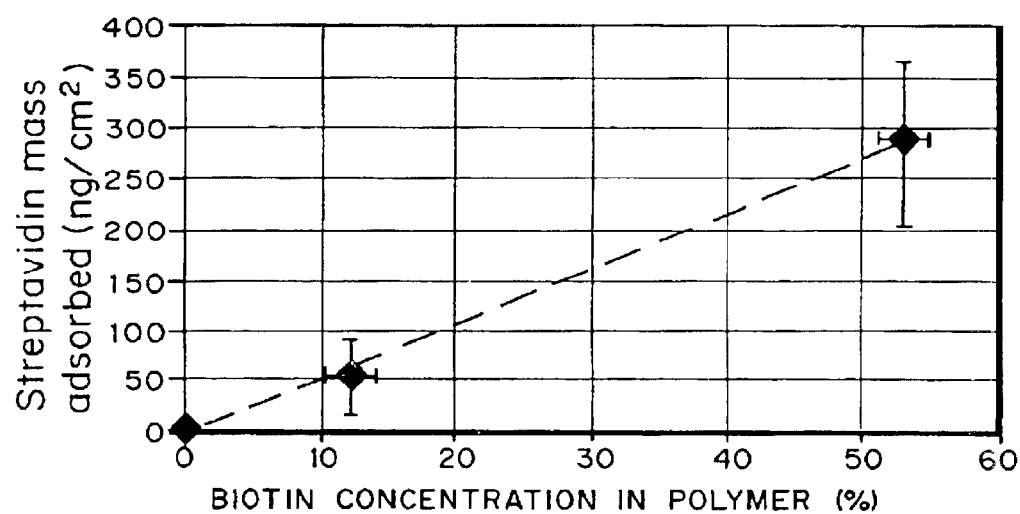
FIG. 12 is a graph of the amount of streptavidin detected by the optical waveguide technique as a function of biotin concentration in the polymer on a chip surface formed of $SixTi1-x O_2$ with adsorbed PLL-g-PEG-biotin.

The first part of the experiment, shown in FIG. 10 demonstrates the protein resistant behavior of the treated oxide surface. Waveguides coated with the PLL-g-PEG-biotin exhibit protein adsorption of less than 2–3 ng/cm$^2$ after exposure to human blood serum. This value is two-hundred-fold lower than the adsorption seen on untreated waveguides. The second part of the experiment demonstrates the specificity of the sensor. A monolayer of streptavidin quickly and irreversibly adsorbs onto the same PLL-g-PEG-biotin functionalized surface after exposure to a 1 mg/ml streptavidin solution. FIG. 11 shows the amount of PLL-g-PEG-biotin adsorbed onto the chip surface and the amount of streptavidin subsequently adsorbed onto the PLL-g-PEG-biotin covered chip surface for three different biotin concentrations in the PLL-g-PEG-biotin molecule (see Table 5). It is obvious that the modified polymer adsorbs onto the chip surface and shows an excellent specificity in the subsequent streptavidin sensing assay. Furthermore, the amount of streptavidin specifically detected is related to the degree of biotinylation. The relation between the amount of streptavidin detected and the biotin surface concentration is linear within the experimental error and in the range of biotin concentrations tested, as shown in FIG. 12.

TABLE 4

PLL quantity and stoichiometric amounts of solid NHS-PEG-biotin and SPA-PEG.

| Polymer | PLL (MW 20'000) | PEG-CH$_3$ (MW 2000) | PEG-biotin (MW 3400) | Lys:PEG expected |
|---|---|---|---|---|
| PLL-g[2]-PEG-OCH$_3$ | 27.2 mg; 1.36 μmol | 123 mg; 65.1 μmol | — | 2 |
| PLL-g[3.5]-PEG-OCH$_3$ | 83.6 mg; 4.18 μmol | 215.7 mg; 114 μmol | — | 3.5 |
| PLL-g[5]-PEG-OCH$_3$ | 106.8 mg; 5.34 μmol | 193.2 mg; 102 μmol | — | 5 |
| PLL-g[3.5]-PEG-Biotin 10%a | 39.5 mg; 1.98 μmol | 92 mg; 48.7 μmol | 18.6 mg 5.4 μmol | 3.5 |
| PLL-g[3.5]-PEG-Biotin 10%b | 39.5 mg; 1.98 μmol | 91.9 mg; 48.7 μmol | 18.6 mg 5.4 μmol | 3.5 |
| PLL-g[3.5]-PEG-Biotin 50% | 32.3 mg; 1.62 μmol | 42 mg; 22.2 μmol | 76 mg; 22.1 μmol | 3.5 |

TABLE 5

Integration values for m-PEG and PEG-biotin. The PLL unit to PEG chains ratio is estimated from the ratio of the integration value of the methyn proton (N—CHR—CO) of the lysine monomer unit to the sum of the proton-weighted integration values of the terminal methoxy protons (O—CH$_3$) from the m-PEG chains and the methylene protons (—CH$_2$—C(O)N—) from the biotin-PEG. The relative amounts of m-PEG and PEG-Biotin are estimated from the same respective integration.

| Polymer | Lys:PEG | PEG-CH$_3$ content [%] | Biotin content [%] |
|---|---|---|---|
| PLL-g[2]-PEG-OCH$_3$ | 2.06 | 100% | 0 |
| PLL-g[3.5]-PEG-OCH$_3$ | 3.43 | 100% | 0 |
| PLL-g[5]-PEG-OCH$_3$ | 5.48 | 100% | 0 |
| PLL-g[3.5]-PEG-Biotin 10%a | 3.9 | 87–90% | 10–13% |
| PLL-g[3.5]-PEG-Biotin 10%b | 3.4 | 86–98% | 11–14% |
| PLL-g[3.5]-PEG-Biotin 50% | 3.1 | 45–49% | 51–55% |

We claim:

1. A method for reducing non-specific adsorption of inorganic ions, peptides, proteins, and saccharides to a surface of a device comprising applying to or coating onto a surface of an analytical or sensing device, wherein the surface comprises a material selected from the group consisting of metals, metal oxides, and charged polymers.

a non-interactive polyionic multifunctional copolymer, wherein the non-interactive polyionic multifunctional copolymer comprises non-interactive polymer sidechains covalently grafted onto a charged polyionic polymeric backbone which has an anionic charge at a pH greater than 4, wherein the polyionic polymeric backbone interacts with the surface at a pH greater than 4, where some or all of the non-interactive polymer sidechains are partially or fully functionalized at or near the free terminal position of the non-interactive polymer sidechains with a functional molecule.

2. The method of claim 1 wherein the functional molecule is selected from the group consisting of protein ligands, polynucleotides, carbohydrate or sugar ligands, simple organic molecules, and cells, and components thereof, and combinations thereof.

3. The method of claim 1 comprising exposing the copolymer to analyte which is bound by the functional molecule in a fluid phase, followed by adsorption of the copolymer onto a substrate or surface.

4. The method of claim 1 comprising exposing the copolymer to analyte which is bound by the functional group, wherein the copolymer is adsorbed onto a substrate or surface.

5. A method for making a biosensing or analytical device having reduced non-specific adsorption of inorganic ions, peptides, proteins and saccharides comprising applying to or coating onto a surface of the biosensing or analytical device non-interactive polyionic multifunctional copolymers, wherein the non-interactive polyionic multifunctional copolymers comprise non-interactive polymer sidechains covalently grafted onto a charged polyionic polymeric backbone, and wherein the surface comprises a material selected from the group consisting of metals, metal oxides, and charged polymers, and the surface of the device has a charge opposite to the charge of the charged polyionic polymeric backbone, and wherein some of the non-interactive polymer side chains comprise a functional moiety and some of the non-interactive polymer side chains do not comprise a functional moiety.

6. The method of claim 5 wherein the functionalized and non-functionalized copolymers are applied sequentially.

7. The method of claim 6 wherein the functionalized copolymers are adsorbed to the surface of the device and exposed to analyte, and wherein non-functionalized copolymers are subsequently adsorbed to the surface.

8. The method of claim 5 wherein the functionalized copolymer is attached to the surface by physisorption or chemisorption.

9. The method of claim 5 wherein the surface is patterned with areas with adsorbed polyionic copolymers not comprising functional groups and areas with adsorbed polyionic copolymers comprising functional groups.

10. The method of claim 9 where the areas have dimensions parallel to the surface in a millimeter, micrometer or submicrometer range.

11. The method of claim 9 where the patterning is done by fluidic, microfluidic, stamping or microcontact printing.

12. The method of claim 9 wherein the polyionic copolymer is applied to the surface, wherein functional molecule is subsequently bound to the copolymer in a defined surface pattern by fluidic, microfluidic, stamping, microcontact printing or ink-jet techniques.

13. The method of claim 9 wherein the non-interactive polymer sidechains are selected from the group consisting of polyethylene glycol, neutral water soluble polysaccharides, polyvinyl alcohol, poloxamer nonionic surfactants; poly-N-vinyl pyrrolidone, non-cationic poly(meth)acrylates, non-cationic polyacrylates, and esters, amides, and hydroxyalky amides thereof.

* * * * *

UNITED STATES PATENT AND TRADEMARK OFFICE
CERTIFICATE OF CORRECTION

PATENT NO. : 6,884,628 B2
APPLICATION NO. : 09/560472
DATED : April 26, 2005
INVENTOR(S) : Jeffrey A. Hubbell et al.

It is certified that error appears in the above-identified patent and that said Letters Patent is hereby corrected as shown below:

On Title page, under "(*) Notice: Subject to any disclaimer, the term of this patent is extended or adjusted under 35 U.S.C. 154 (b) by 393 days.", the statement "This patent is subject to a terminal disclaimer." should be deleted.

Claim 13, column 44, line 39 the semi-colon ";" between "surfactants" and "poly-N-" should be deleted and replaced with a comma ",".

Signed and Sealed this

Seventh Day of April, 2009

JOHN DOLL
*Acting Director of the United States Patent and Trademark Office*